US012647349B2

(12) United States Patent
Li et al.

(10) Patent No.: US 12,647,349 B2
(45) Date of Patent: Jun. 2, 2026

(54) METHODS AND DEVICES FOR DATA TRANSMISSION

(71) Applicant: SHANGHAI UNITED IMAGING HEALTHCARE CO., LTD., Shanghai (CN)

(72) Inventors: Linfeng Li, Shanghai (CN); Hongtao Wang, Shanghai (CN); Haiyun Hou, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 311 days.

(21) Appl. No.: 18/427,777

(22) Filed: Jan. 30, 2024

(65) Prior Publication Data

US 2024/0171502 A1     May 23, 2024

Related U.S. Application Data

(63) Continuation of application No. PCT/CN2022/111476, filed on Aug. 10, 2022.

(30) Foreign Application Priority Data

Aug. 10, 2021     (CN) .......................... 202110913777.7

(51) Int. Cl.
*H04L 45/00*          (2022.01)
*A61B 6/00*           (2006.01)
*H04L 45/28*          (2022.01)

(52) U.S. Cl.
CPC .............. *H04L 45/22* (2013.01); *A61B 6/563* (2013.01); *H04L 45/28* (2013.01)

(58) Field of Classification Search
None
See application file for complete search history.

(56) References Cited

U.S. PATENT DOCUMENTS

| | | | |
|---|---|---|---|
| 2003/0002617 A1 | 1/2003 | Hsieh et al. | |
| 2006/0114818 A1* | 6/2006 | Canali ................. | H04L 43/0811 370/242 |

(Continued)

FOREIGN PATENT DOCUMENTS

| | | |
|---|---|---|
| CN | 104407540 A | 3/2015 |
| CN | 104545981 A | 4/2015 |

(Continued)

OTHER PUBLICATIONS

The Extended European Search Report in European Application No. 22855472.1 mailed on Sep. 19, 2024, 7 pages.

(Continued)

*Primary Examiner* — Angela Nguyen
(74) *Attorney, Agent, or Firm* — METIS IP LLC

(57)          ABSTRACT

The present disclosure relates to methods and devices for data transmission. The methods is implemented on a data processing unit (220) of a computed tomography (CT) device, the data processing unit (220) is communicatively connected to a plurality of first communication links and at least one second communication link. The method comprises: determining, whether a first communication link group includes at least one failed communication link, the first communication link group including the plurality of first communication links; in response to determining that the first communication link group includes at least one failed communication link, selecting, from the at least one second communication link, at least one target communication link matching the at least one failed communication link; and adjusting the first communication link group to a second communication link group, and the second communication link group including at least the at least one target communication link.

20 Claims, 13 Drawing Sheets

(56) References Cited

U.S. PATENT DOCUMENTS

| | | | |
|---|---|---|---|
| 2010/0162033 A1 | 6/2010 | Ahn et al. | |
| 2010/0193699 A1 | 8/2010 | Hattori et al. | |
| 2011/0150171 A1 | 6/2011 | Breuer et al. | |
| 2012/0163163 A1* | 6/2012 | Kim .................... | H04L 41/0663 |
| | | | 370/218 |
| 2014/0126355 A1* | 5/2014 | Filsfils ................ | H04L 12/4645 |
| | | | 370/225 |
| 2016/0219686 A1 | 7/2016 | Nakayama et al. | |
| 2019/0034305 A1 | 1/2019 | Perumal et al. | |
| 2019/0107637 A1 | 4/2019 | Nelson et al. | |

FOREIGN PATENT DOCUMENTS

| | | | |
|---|---|---|---|
| CN | 204542169 U | 8/2015 | |
| CN | 207439973 U | 6/2018 | |
| CN | 109412920 A | 3/2019 | |
| CN | 110661702 A | 1/2020 | |
| CN | 111193664 A | 5/2020 | |
| CN | 112263264 A | 1/2021 | |
| JP | 2003019127 A | 1/2003 | |
| JP | 2005253627 A | 9/2005 | |
| JP | 2013063153 A | 4/2013 | |
| JP | 5348923 B2 | 11/2013 | |
| JP | 2018007944 A | 1/2018 | |
| JP | 2020141721 A | 9/2020 | |
| WO | 2020234143 A1 | 11/2020 | |
| WO | 2023016492 A1 | 2/2023 | |

OTHER PUBLICATIONS

International Search Report in PCT/CN2022/111476 mailed on Oct. 28, 2022, 4 pages.

Written Opinion in PCT/CN2022/111476 mailed on Oct. 28, 2022, 5 pages.

First Office Action in Chinese Application No. 202110913777.7 mailed on Apr. 14, 2023, 22 pages.

\* cited by examiner

100

Data processing unit 220

Obtaining  Module 310

Determination Module 320

Selection Module 330

Adjustment Module 340

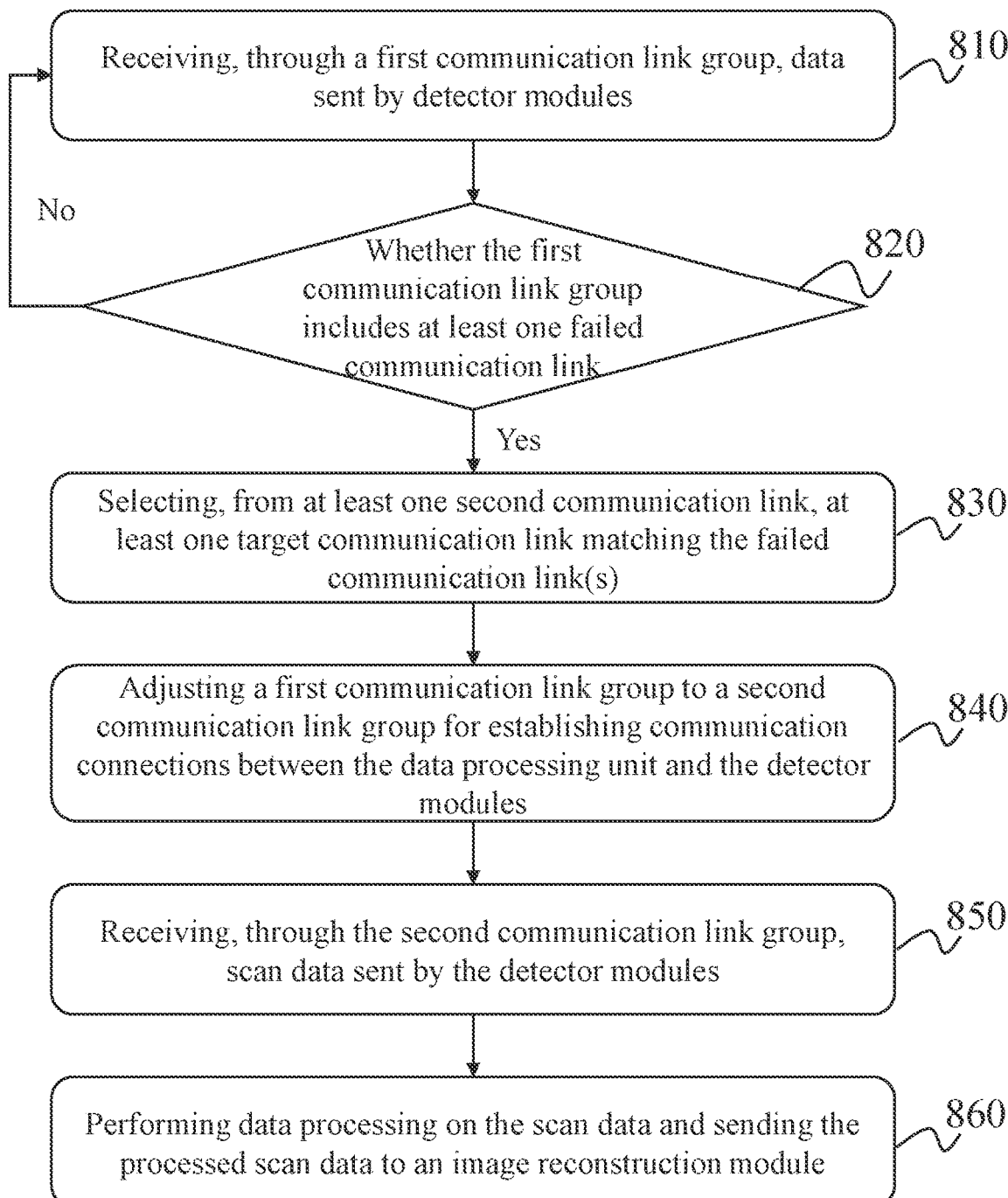

Receiving, through a first communication link group, data sent by detector modules 810

Whether the first communication link group includes at least one failed communication link 820

No

Yes

Selecting, from at least one second communication link, at least one target communication link matching the failed communication link(s) 830

Adjusting a first communication link group to a second communication link group for establishing communication connections between the data processing unit and the detector modules 840

Receiving, through the second communication link group, scan data sent by the detector modules 850

Performing data processing on the scan data and sending the processed scan data to an image reconstruction module 860

FIG. 8

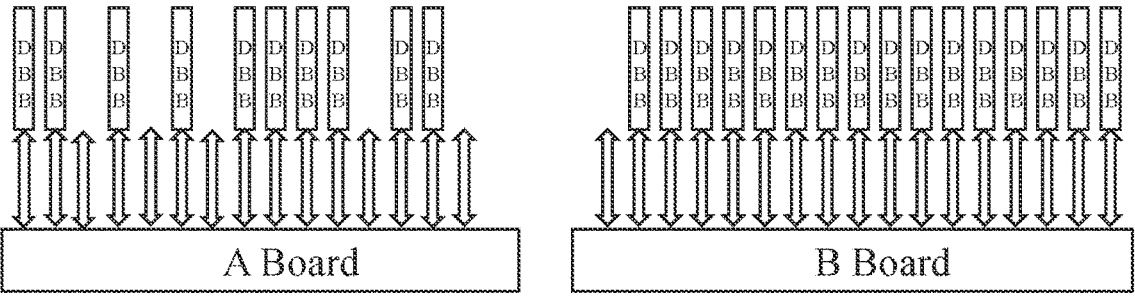
(a)
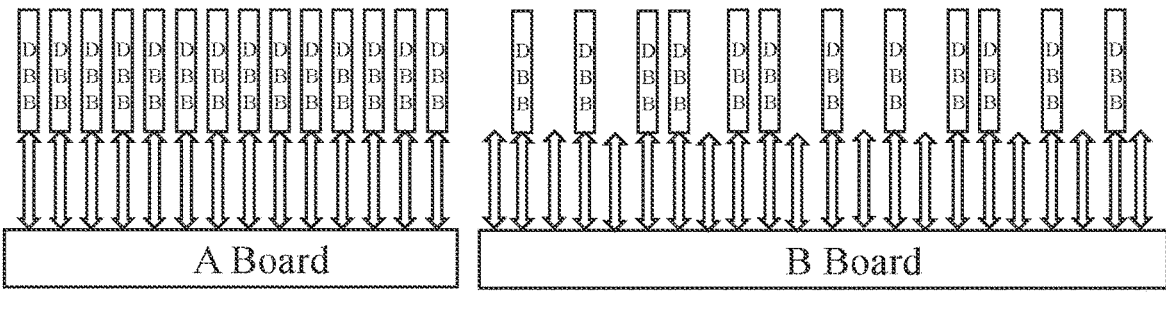
(b)
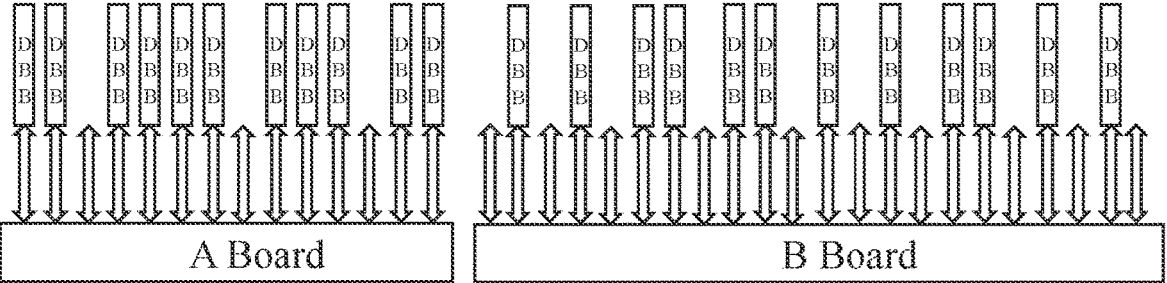
(c)
FIG. 11

METHODS AND DEVICES FOR DATA TRANSMISSION

CROSS-REFERENCE TO RELATED APPLICATIONS

This application is a Continuation of International Application No. PCT/CN2022/111476, filed on Aug. 10, 2022, which claims priority of Chinese Patent Application No. 202110913777.7 filed on Aug. 10, 2021, the contents of which are hereby incorporated by reference.

TECHNICAL FIELD

This disclosure relates to the field of data transmission, in particular to methods and devices for transmitting computed tomography (CT) scan data.

BACKGROUND

In an imaging process performed by a CT device, photocurrents are collected by a plurality of detector modules and converted into digital signals, and then the digital signals are transmitted to a data processing unit (such as a data processing board) through fixed data transmission channels corresponding to the plurality of detector modules one by one, and then image reconstruction may be carried out to obtain a medical image. However, once any one of the data transmission channels fails, the CT device will not be able to continue scanning. In such cases, in order to repair the failed data transmission channel, all the data transmission channels may need to be adjusted and debugged.

Thus, it is desirable to provide systems and methods for transmitting CT scan data, which can shorten the fault repair time, and improve the scanning efficiency.

SUMMARY

An aspect of the present disclosure relates to a method for data transmission. Wherein the method is implemented on a data processing unit (220) of a computed tomography (CT) device, the data processing unit (220) is communicatively connected to a first communication link group and at least one second communication link. The method comprises: determining, whether the first communication link group includes at least one failed communication link; in response to determining that the first communication link group includes at least one failed communication link, selecting, from the at least one second communication link, at least one target communication link matching the at least one failed communication link; and adjusting the first communication link group to a second communication link group, and the second communication link group at least including the at least one target communication link.

A further aspect of the present disclosure relates to a computed tomography (CT) device. The device comprising: a scanner configured to scan a target object; a detector (112) configured to acquire scan data, the detector (112) including a plurality of detector modules; a data transmission device (160) configured to perform data processing on the scan data; and an image reconstruction unit configured to perform image reconstruction on the processed scan data, so as to generate a scanned image of the target object, wherein the data transmission device (160) include a plurality of communication links and a data processing unit (220), wherein the data processing unit (220) is communicatively connected to a plurality of first communication links and at least one second communication link, the plurality of first communication links are configured to establish a plurality of communication connections between the data processing unit (220) and the plurality of detector modules, and the at least one second communication link is configured to replace at least one failed communication link when the plurality of first communication links include the at least one failed communication link.

A still further aspect of the present disclosure relates to a device for data transmission (160). Wherein the device (160) is implemented on a computed tomography (CT) device, and the device (160) comprises: a data processing unit (220) being communicatively connected to a first communication link group and at least one second communication link, wherein the data processing unit (220) is configured to: determine, whether the first communication link group includes at least one failed communication link; in response to determining that the first communication link group includes at least one failed communication link, select, from the at least one second communication link, at least one target communication link matching the at least one failed communication link; and adjust the first communication link group to a second communication link group, and the second communication link group at least including the at least one target communication link.

A still further aspect of the present disclosure relates to a non-transitory computer readable medium, comprising at least one set of instructions. Wherein when executed by at least one processor, the at least one set of instructions directs the at least one processor to perform a method for data transmission. The method comprises: determining, whether a first communication link group includes at least one failed communication link; in response to determining that the first communication link group includes at least one failed communication link, selecting, from at least one second communication link, at least one target communication link matching the at least one failed communication link; and adjusting the first communication link group to a second communication link group, and the second communication link group at least including the at least one target communication link.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3 is a block diagram illustrating an exemplary data processing unit according to some embodiments of the present disclosure;

FIG. 8 is an exemplary flowchart illustrating an exemplary process for data transmission according to some embodiments of the present disclosure;

FIG. 11 is a schematic diagram illustrating data processing boards according to some embodiments of the present disclosure;

DETAILED DESCRIPTION

Figure 1:
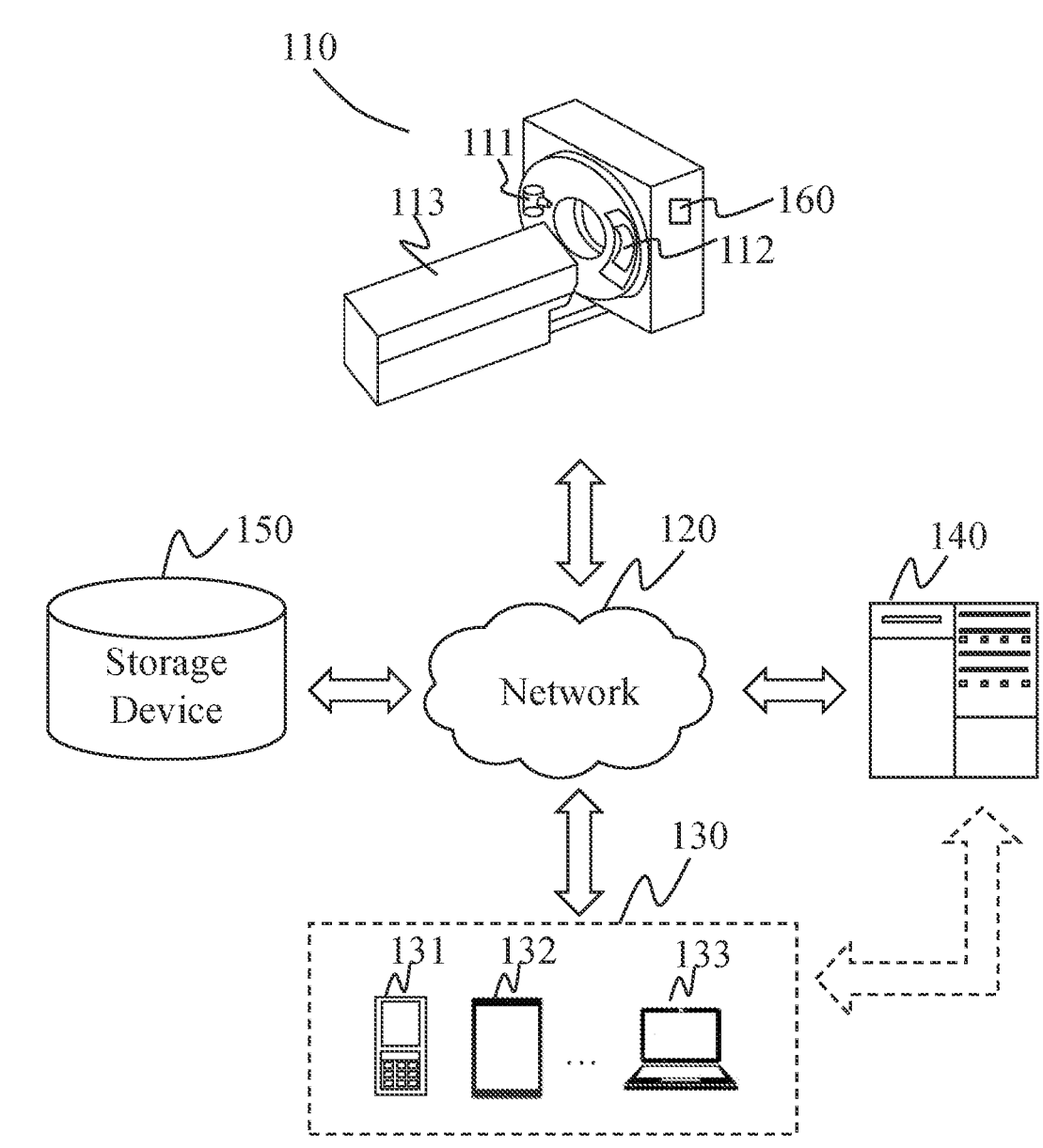
FIG. 1 is a schematic diagram illustrating an exemplary data transmission system according to some embodiments of the present disclosure.

In order to more clearly explain the technical scheme of the embodiment of the present disclosure, the drawings required in the description of the embodiment are briefly introduced below. Obviously, the drawings in the following description are only some examples or embodiments of the present disclosure. For those skilled in the art, the present disclosure can also be applied to other similar situations according to these drawings without paying creative labor. Unless obviously obtained from the context or the context illustrates otherwise, the same numeral in the drawings refers to the same structure or operation.

It should be understood that the "system", "device", "unit" and/or "module" used herein is a method for distinguishing different components, elements, components, parts, or assemblies at different levels. However, if other words may achieve the same purpose, the words may be replaced by other expressions.

As shown in the present disclosure and claims, unless context clearly prompts the exception, "a", "one", and/or "the" is not specifically singular, and the plural may be included. In general, the terms "comprises" "comprising" "includes" and/or "including" only indicate that the steps and units that have been clearly identified are included, the steps and units do not constitute an exclusive list, and the method or device may also include other steps or units.

The flowcharts are used in the present disclosure to illustrate operations performed by the system according to the embodiment of the present disclosure. It should be understood that the foregoing or following operations may not be necessarily performed exactly in order. Instead, each operation may be processed in reverse or simultaneously.

Moreover, other operations may also be added into these procedures, or one or more steps may be removed from these procedures.

In a CT device, a plurality of detector modules and one or more data processing boards are interconnected by high-speed cables. The use of a large number of cables has high requirements for machine assembly, and when a gantry of the CT device rotates with a high-speed (e.g., a speed exceeding a threshold), it is easy to cause poor contact or mechanical fatigue and other failures of a connector. Once the connection between the detector modules and the data processing board(s) has a failure, it needs to be handled manually. The deployment and replacement of failed parts take a long time, which affects the use efficiency, the user experience, and the public praise of the CT device. Therefore, a reliable connector between the detector modules and the data processing board(s) and a reliable data transmission method are needed.

Some embodiments of the present disclosure provide methods for data transmission, which may be used for transmitting CT scan data and other data. Specifically, when it is detected that there is at least one failed communication link in the first communication link group, at least one target communication link matching the failed communication link(s) may be automatically selected from at least one second communication link connected with the data processing unit, and the first communication link group may be adjusted to a second communication link group for establishing the communication connections between the data processing unit and data sending units. The method for data transmission in the present disclosure can not only improve the reliability and stability of data transmission, but also have almost no additional cost, and provide new technical means for service engineers to deal with communication failures and other problems.

FIG. 1 is a schematic diagram illustrating an exemplary data transmission system according to some embodiments of the present disclosure.

As shown in FIG. 1, in some embodiments, a data transmission system 100 may include a scanning device 110, a network 120, a terminal 130, a processing device 140, a storage device 150, and a data transmission device 160. In some embodiments, the data transmission system 100 may be configured to implement the methods for scan data transmission provided in the embodiments of the present disclosure. For example, the data transmission device 160 may receive scan data sent by detector modules of the scanning device 110, perform a data processing on the scan data, and send the processed scan data to the processing device 140 to perform reconstruction and/or analysis on the processed scan data. It should be understood that the data transmission system 100 may also be used for transmitting other data (such as video surveillance data), and the scan data is only an example provided for illustrative purposes.

The scanning device 110 may be configured to scan a target object or a part thereof located in a detection area of the scanning device 110 and generate scan data (also referred to as image data) related to the target object or part thereof. In some embodiments, the target object may include a body, a substance, or the like, or any combination thereof. In some embodiments, the target object may include a specific part of a human body, such as the head, the chest, the abdomen, or the like, or any combination thereof. In some embodiments, the target object may include specific organs, such as the heart, the esophagus, the trachea, the bronchus, the stomach, the gallbladder, the small intestine, the colon, the bladder, the ureter, the uterus, the fallopian tube, or the like. In some embodiments, the target object may include a patient or another medical experimental object (for example, an animal such as an experimental mouse).

For example, the scanning device 110 may include a CT device. As shown in FIG. 1, the scanning device 110 may include a radiation source 111, a detector 112, and a scanning bed 113. The radiation source 111 may be configured to emit radiation beams. The detector 112 may be configured to detect the radiation beams. The radiation source 111 may emit radiation beams (E. G., X-ray) to the target object (E. G., the breast), and the radiation beams may be attenuated by the target object and detected by the detector 112, thereby generating image signals.

Figure 5:
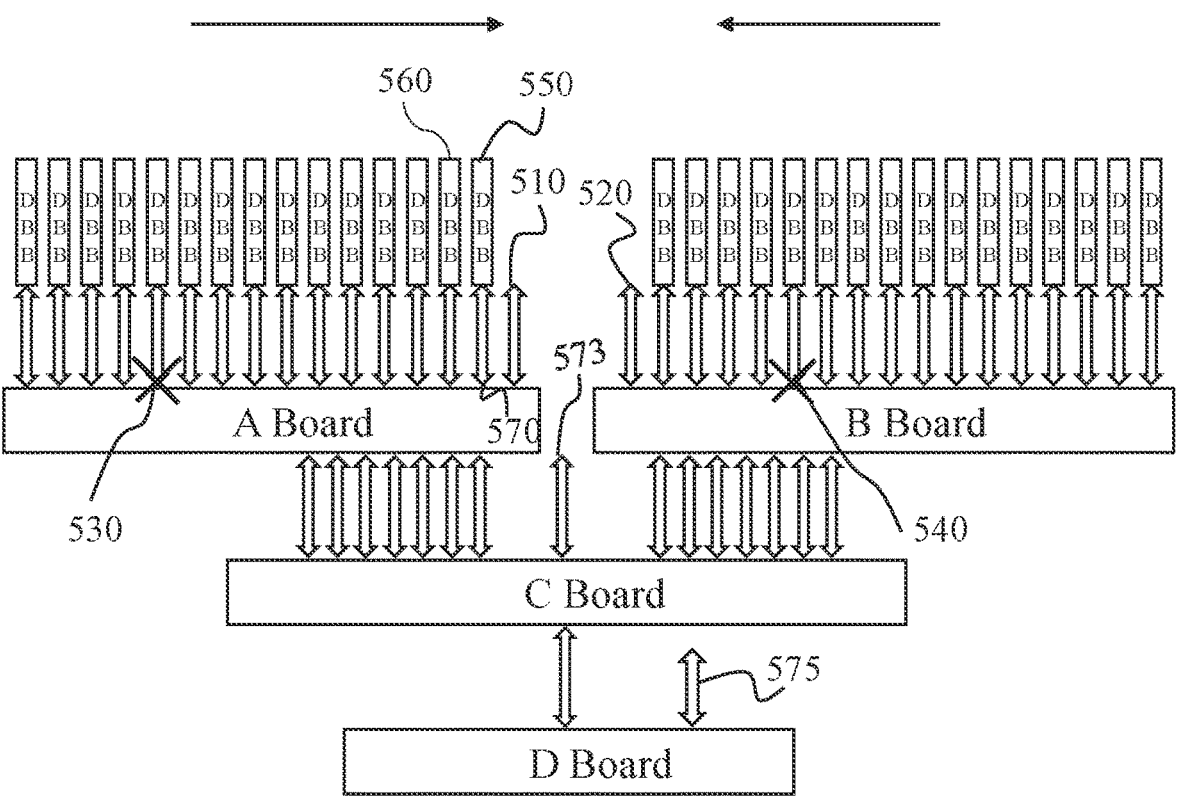
FIG. 5 is a schematic diagram illustrating an exemplary data transmission device according to some embodiments of the present disclosure.
Figure 6:
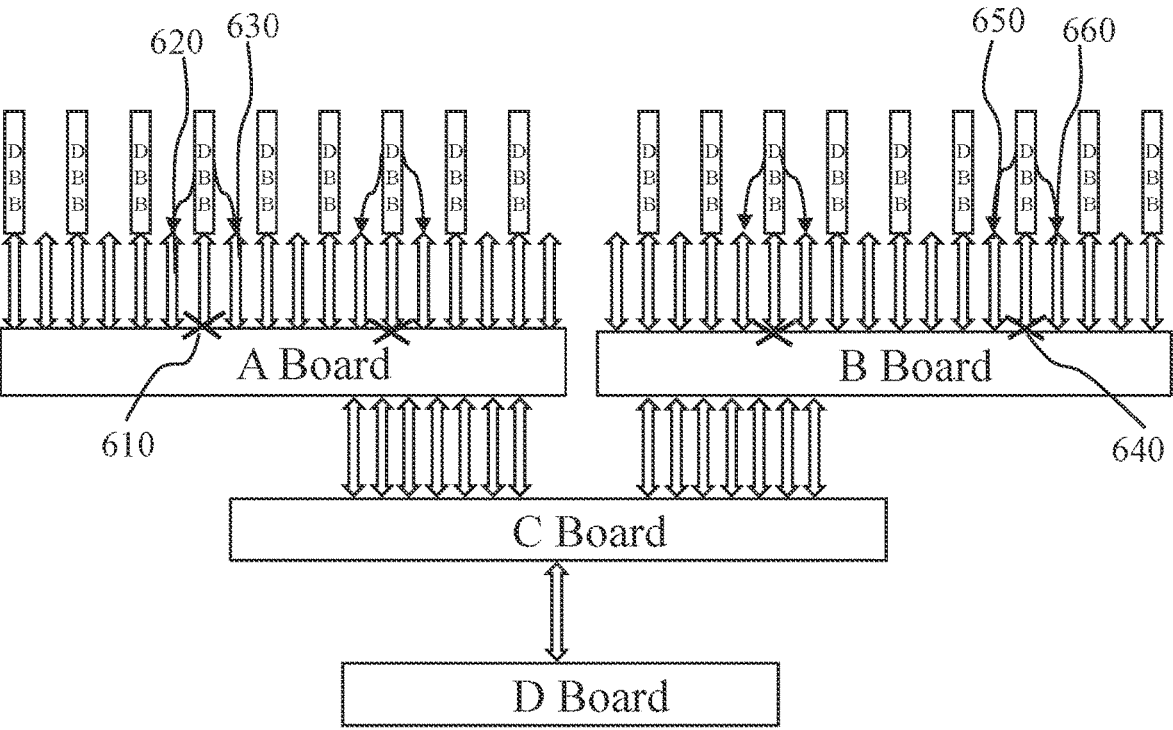
FIG. 6 is a schematic diagram illustrating an exemplary data transmission device according to some embodiments of the present disclosure.
Figure 7:
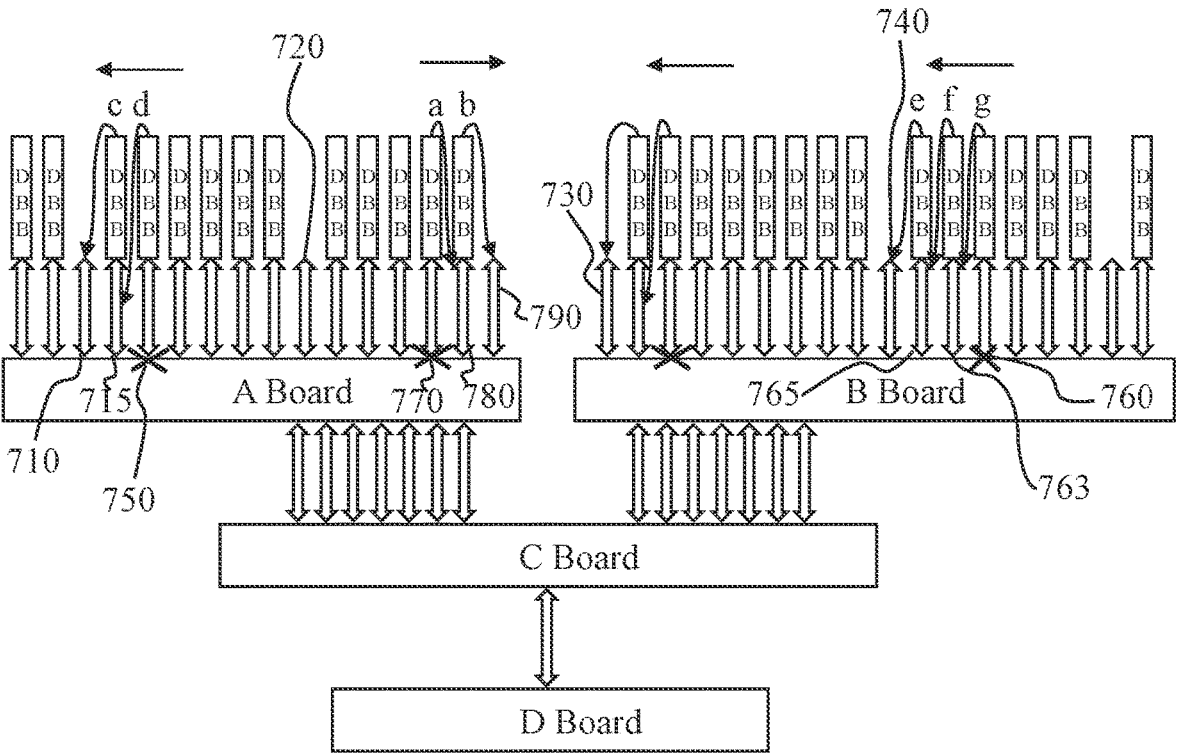
FIG. 7 is a schematic diagram illustrating an exemplary data transmission device according to some embodiments of the present disclosure.

In some embodiments, the detector 112 may include one or more detector modules, such as a plurality of DBBs shown in FIGS. 5-7. In some embodiments, a detector module may include a single row of detectors and/or multiple rows of detectors. In some embodiments, a detector module may include a scintillation detector (e.g., a cesium iodide detector) or another detector. In some embodiments, one or more detector modules of the detector 112 may serve as a data sending device and be connected to the data transmission device 160. The scan data collected by the detector module(s) may be processed by the data transmission device 160 and transmitted to the processing device 140 to perform image data reconstruction and/or analysis.

In some embodiments, the scanning device 110 may include, for example, a positron emission computed tomography (PET) scanning device, a magnetic resonance imaging (MRI) scanning device, an X-ray scanning device, a CT device, and other single-modality scanning devices. In some embodiments, the scanning device 110 may include, for example, an X-ray imaging-magnetic resonance imaging (X-ray-MRI) scanning device, a positron emission tomography-X-ray imaging (PET-X-ray) scanning device, a single photon emission computed tomography-magnetic resonance imaging (SPECT-MRI) scanning device, and a positron emission tomography-computer tomography (PET-CT) scanning device, and other multi-modality scanning devices.

The network 120 may include any suitable network capable of facilitating an exchange of information and/or data of the data transmission system 100. In some embodiments, one or more components of the data transmission system 100 (e.g., the scanning device 110, the terminal 130, the processing device 140, the storage device 150, etc.) may exchange information and/or data with one or more components of the data transmission system 100 through the network 120.

In some embodiments, the network 120 may include a public network (such as the Internet), a private network (such as a local area network (LAN), a wide area network (WAN)), a wired network (such as Ethernet), a wireless network (such as an 802.11 network, a wireless Wi-Fi network, etc.), a hive network (such as a long term evolution (LTE) network), a frame relay network, a virtual private network (VPN), a satellite network, a telephone network, a router a hub, a server computer, etc., or any combination thereof. For example, the network 120 may include a wired network, an optical fiber network, a telecommunications network, a local area network, a wireless local area network (WLAN), a metropolitan area network (MAN), a public switched telephone network (PSTN), and a Bluetooth™ network, a ZigBee™ network, a near field communication (NFC) network, etc., or any combination thereof. In some embodiments, network 120 may include one or more network access points. For example, the network 120 may include wired and/or wireless network access points, such as base stations and/or Internet switching points, through the access points one or more components of the data transmission system 100 may connect to the network 120 to exchange data and/or information.

In some embodiments, the terminal 130 may interact with other components in the data transmission system 100 through the network 120. For example, the terminal 130 may send one or more control instructions to the scanning device 110 through the network 120 to control the scanning device 110 to scan the target object according to the instructions. In some embodiments, the terminal 130 may include a mobile device 131, a tablet 132, a laptop 133, etc., or any combination thereof. For example, the mobile device 131 may include a smart home device, a wearable device, a mobile device, a virtual reality device, an augmented reality device, etc., or any combination thereof.

In some embodiments, the terminal 130 may be part of the processing device 140. In some embodiments, the terminal 130 may be integrated with the processing device 140 as an operation platform of the scanning device 110. For example, a user/operator of the data transmission system 100 (E. G., a doctor or a nurse) may control an operation of the scanning device 110 through operation platform, such as scanning the target object, controlling a movement of the scanning bed 113, and so on.

The processing device 140 may process data and/or information obtained from the scanning device 110, the terminal 130, and/or the storage device 150. For example, the processing device 140 may receive the scan data collected by the scanning device 110 from the data transmission device 160 and process the scan data. As an example only, the processing device 140 may reconstruct a reconstructed image of the target object based on the scan data.

In some embodiments, the processing device 140 may be a single server or a group of servers. The group of servers may be centralized or distributed. In some embodiments, the processing device 140 may be local or remote. For example, the processing device 140 may access information and/or data from the scanning device 110, the terminal 130, and/or the storage device 150 through the network 120. As another example, the processing device 140 may be directly connected to the scanning device 110, the terminal 130, and/or the storage device 150 to access information and/or data. In some embodiments, the processing device 140 may be implemented on a cloud platform. For example, the cloud platform may include one or more combinations of a private cloud, a public cloud, a hybrid cloud, a community cloud, a distributed cloud, a cross cloud, a multi cloud, etc., or any combination thereof.

The storage device 150 may store data, instructions, and/or any other information. In some embodiments, the storage device 150 may store data obtained from the scanning device 110, the terminal 130, and/or the processing device 140. In some embodiments, the storage device 150 may store data and/or instructions that the processing device 140 may execute or use to perform the exemplary process described in the present disclosure.

In some embodiments, the storage device 150 may include a mass memory, a removable memory, a volatile read-write memory, a read-only memory (ROM), etc., or any combination thereof. In some embodiments, the storage device 150 may be implemented through a cloud platform described in the present disclosure.

In some embodiments, the storage device 150 may be connected to the network 120 to achieve communication with one or more components (e.g., the processing device 140, the terminal 130, etc.) in the data transmission system

100. One or more components in the data transmission system 100 may read data or instructions in the storage device 150 through the network 120. In some embodiments, the storage device 150 may be part of the processing device 140 or may be independent and directly or indirectly connected to the processing device 140.

The data transmission device 160 may be configured to transmit and process the scan data collected by the detector 112. For example, the data transmission device 160 may receive scan data sent by the detector modules, perform data processing on the scan data, and send the processed scan data to the processing device 140 to perform reconstruction and/or analysis on the processed scan data. In some embodiments, the data transmission device 160 may transmit the scan data to the data processing device 140 without processing the scan data. In some embodiments, the data transmission device 160 may include a data processing unit and a plurality of communication links connected to the data processing unit. For example, the data processing unit may be communicatively connected with a plurality of first communication links and one or more second communication links. The first communication links may be used to establish a communication connection between the data processing unit and the detector 112, and the second communication link(s) may be used to replace one or more failed communication link when the first communication links include the failed communication link(s). For example, the data processing unit may establish the communication connection with the detector modules of the detector 112 through the first communication links to receive the scan data sent by the detector 112. It should be noted that the above data transmission system 100 and its related description are provided for illustrative purposes only and are not intended to limit the scope of the present disclosure. For those skilled in the art, various modifications or changes can be made according to the description of the present disclosure. For example, the data transmission system 100 may also include a display device. As another example, each component of the data transmission system 100 may have its storage device, or jointly use one storage device. However, these changes and modifications will not deviate from the scope of the present disclosure.

Figure 2:
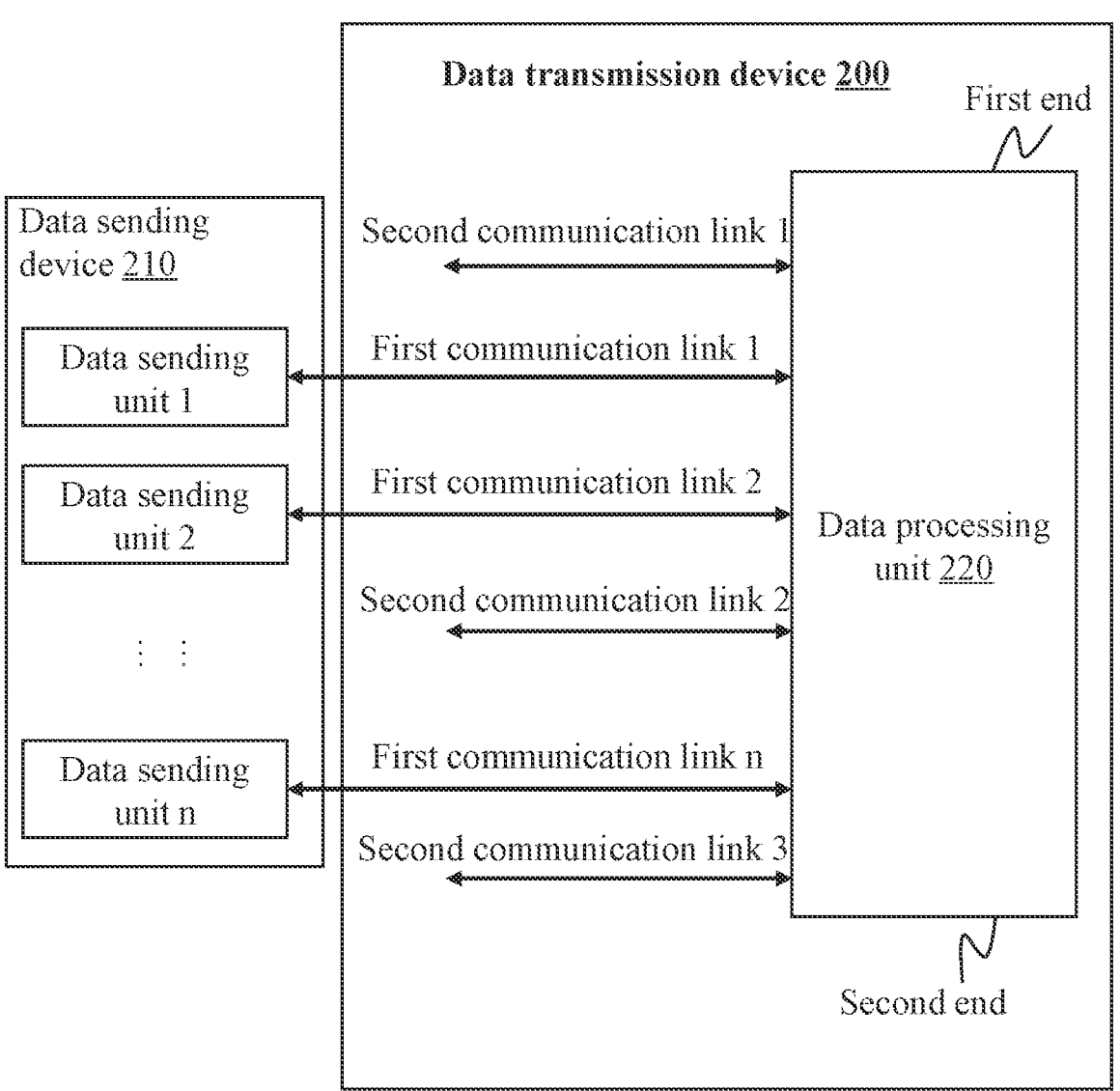
FIG. 2 is a schematic diagram illustrating an exemplary data transmission device according to some embodiments of the present disclosure.

FIG. 2 is a schematic diagram illustrating an exemplary data transmission device according to some embodiments of the present disclosure. The data transmission device 200 shown in FIG. 2 may be an embodiment of the data transmission device 160 shown in FIG. 1.

As shown in FIG. 2, the data transmission device 200 may be communicatively connected to a data sending device 210. In some embodiments, the data sending device 210 may include a plurality of data sending units, for example, a data sending unit 1, a data sending unit 2, . . . , and a data sending unit n. The data sending units may include any component that is capable of sending data. In some embodiments, the data sending units may include a plurality of detector modules of a CT device. For example, as shown in FIG. 5 to FIG. 7, a data sending unit may include a DBB (Detector Building Block). In some embodiments, the data sending device 210 may include communication interfaces or communication ports of at least one data processing board. For example, as shown in FIG. 5 to FIG. 7, the data sending device 210 may include A Board, B Board, or C board, and the data sending units may include communication ports of these data processing boards.

The data transmission device 200 may include a plurality of communication links and a data processing unit 220. Each of the communication links may be communicatively connected to the data processing unit 220. In some embodiments, the communication links may include one or more first communication links and one or more second communication links. The data sending device 210 may be communicatively connected to the data processing unit 220 through the first communication link(s).

In some embodiments, each of the first communication links may be communicatively connected to a data sending unit of the data sending device 210. For example, the data sending unit 1 may be communicatively connected to the data processing unit 220 through a first communication link 1, the data sending unit 2 may be communicatively connected to the data processing unit 220 through a first communication link 2, . . . , and the data sending unit n may be communicatively connected to the data processing unit 220 through the first communication link n. In some embodiments, the data sending units may be communicatively connected to the data processing unit 220 through a short distance non-contact communication mode. The short distance may refer to that a signal coverage area of a communication connection interface is less than a specific value. For example, the signal coverage area may be less than 8 mm, 10 mm, 15 mm, or the like. As another example, the short distance non-contact communication mode may include Near Field Communication (NFC), Bluetooth, Radio Frequency Identification (RFID), or the like. In some embodiments, a maximum communication rate of the short distance non-contact communication mode may be 6 Gb/s. In some embodiments, the data sending units may be communicatively connected to the data processing unit 220 through a plurality of cables (e.g., fiber optics, metal cables).

In some embodiments, the data processing unit 220 may be communicatively connected to a plurality of first communication links (e.g., the first communication link 1, the first communication link 2, . . . , and the first communication link n) and at least one second communication link (e.g., a second communication link 1, a second communication link 2, and a second communication link 3). The first communication links may be configured to establish the communication connections between the data processing unit 220 and the data sending device 210. The second communication link(s) may be backup communication link(s). When the first communication links include at least one failed communication link, the second communication link(s) may be configured to replace the at least one failed communication link. For example, when the data processing unit 220 detects that the first communication link(s) include the failed communication link(s), the data processing unit 220 may select at least one target communication link matching the failed communication link(s) from the second communication link(s), and obtain identification(s) of the target communication link(s). The data processing unit 220 may adjust a first communication link group to a second communication link group for establishing the communication connections between the data processing unit 220 and the data sending units based on the identification(s) of the target communication link(s). The data processing unit 220 may further receive scan data sent by the data sending device 210 through the second communication link group.

In some embodiments, the second communication link(s) may include one or more second communication links that are closer to an edge of the data processing unit 220 than the first communication links. In some embodiments, the second communication link(s) may include a plurality of second communication links arranged at intervals with the first communication links. For example, as shown in FIG. 2, the second communication link 1 is closer to a first end of the data processing unit 220 than the first communication links 1-*n*, the second communication link 3 is closer to a second end of the data processing unit 220 than the first communication links 1-*n*. As another example, the second communication link 1, the second communication link 2, and the second communication link 3 are arranged at intervals with the first communication link 1, the first communication link 2, . . . , and the first communication link n. The second communication link 1, the second communication link 2, and the second communication link 3 may be exemplary examples. The second communication link(s) may include any count of second communication links. In some embodiments, a count of the second communication link(s) may be equal or not equal to a count of the first communication links.

In some embodiments, the data processing unit 220 may include at least two data processing boards. The data processing boards may be combined to form a data processing board array. The structure of the data processing board array may match the structure of an arc detector array that is formed by a plurality of detector modules of the CT device. For example, the data processing unit 220 may include a pair of arc boards with the same arc degree and the same size. An arc structure or a circular structure matching the arc detector array may be formed by connecting the pair of arc boards with each other from end to end.

In some embodiments, the data processing unit 220 may include a pair of data processing boards. The structures of the data processing boards in the pair may be symmetrical, A Board and B Board are shown in FIG. 5 to FIG. 7. By setting the data processing boards in the pair to be with the symmetrical structures, the production efficiency of the data processing boards may be improved, thereby avoiding a complex processing flow that is caused by producing asymmetrical data processing boards with different structures, low production efficiency, and increased production costs.

In some embodiments, the data processing unit 220 may include two or more than two data processing boards with different sizes or the same size, A Board and B Board are shown in FIG. 11(*b*) and FIG. 11(*c*). The two or more than two data processing boards may form a data processing board array that matches the structure of the arc detector array including the detector modules of the CT device.

In some embodiments, a communication link (e.g., a first communication link, a second communication link) may be an interface of a data processing board or mounted on the data processing board. For example, a first communication link may be an interface of a data processing board corresponding to one detector module of the CT device. A second communication link may be a backup interface of the data processing board. In some embodiments, a second communication link may be a preset idle interface of the data processing board. For example, the data processing board may include a plurality of interfaces based on a factory setting. A portion of the interfaces may be communicatively connected to the detector modules of the CT device, and the remaining portion of the interfaces may be the idle interface(s). In some embodiments, a second communication link may be an idle interface of a connector connected to the data processing board. In some embodiments, the data processing unit 220 may include a Field Programmable Gate Array (FPGA) processor.

In some embodiments, the data processing unit 220 may include at least two data processing boards, and the second communication link(s) may be communicatively connected to at least one of the at least two data processing boards. In some embodiments, different data processing boards may be connected to the same count of second communication links. As shown in FIG. 5, the two data processing boards A and B are communicatively connected to twenty second communication links, respectively. In some embodiments, different data processing boards may be connected to the different counts of second communication links. As shown in FIG. 11(*a*), the data processing unit 220 may include a data processing board A and a data processing board B having symmetrical structures, the data processing board A may be connected to a first count (e.g., four) of second communication links, and the data processing board B may be connected to a second count (e.g., one) of second communication links. As shown in FIG. 11(*b*), the data processing unit 220 may include a data processing board A and a data processing board B having asymmetrical structures, the data processing board A may not be connected to any second communication links, and the data processing board B may be connected to nine second communication links. As shown in FIG. 11(*c*), the data processing unit 220 may include a data processing board A and a data processing board B having asymmetrical structures, the data processing board A may be connected to a first count (e.g., three) of second communication links, and the data processing board B may be connected to a second count (e.g., ten) of second communication links. The data processing boards connecting to different counts of second communication link may be used to satisfy the requirements of special cases. For example, when a loss rate of the data processing board X is different from a loss rate of the data processing board Y due to external environmental factors, the first count and the second count may be adjusted accordingly. For example, a ratio of the first count to the second count may be equal to a ratio of the loss rate of the data processing board X to the loss rate of the data processing board Y.

In some embodiments, the count of the second communication link(s) that is connected to a data processing board may be adjusted to any value based on actual conditions. In some embodiments, a count and/or an arrangement manner of the second communication link(s) that is connected to the data processing board may be determined based on a probability that the data processing board has a communication link failure, such as shown in FIG. 11(*a*) to FIG. 11(*c*). For example, a count of historical communication link failures that the data processing board has may be determined based on historical data of the CT device. If the count of historical communication link failures is greater than a threshold, more second communication links may be arranged on the data processing board to be used as backup communication links. As another example, positions where the historical communication link failures occur may be determined, and one or more second communication links may be arranged close to the positions.

In some embodiments, a count and/or an arrangement manner of the second communication link(s) that is connected to the data processing board may be determined based on a trained first machine learning model. For example, the first machine learning model may include a Convolutional Neural Network (CNN), a Recurrent Neural Network (RNN), a Deep Neural Networks (DNN), or the like. For example, an input of the first machine learning model may include related information (e.g., a type, a size, a count of historical failures, etc.) of the data processing board(s) and/or related information (e.g., a quantity and a location) of the first communication links, and an output of the first machine learning model may include a count and/or a location of the second communication link(s).

The first machine learning model may be obtained based on first training samples with labels. For example, related information (e.g., a type, a size, a count of historical failures, etc.) of a plurality of sample data processing board(s) may be obtained. Related information (e.g., a count and locations) of sample first communication links and sample second communication link(s) connected to each sample data processing board may also be obtained. The label of each first training sample may be determined based on related information of the sample second communication link(s) of the first training sample. The plurality of first training samples with labels may be input into a first preliminary machine learning model. A first loss function may be determined based on the labels and a predicted result output by the first preliminary machine learning model. Parameters of the first preliminary machine learning model may be iteratively updated by gradient descent or other methods based on the first loss function. The training of the first machine learning model may be terminated when a preset condition is satisfied, and the trained first machine learning model may be obtained. The preset condition may include that the first loss function converges (e.g., having a value lower than a threshold), that a count of iterations reaches a threshold, or the like.

In some embodiments, a count and/or an arrangement manner of the second communication link(s) may be determined based on a probability that a communication link failure occurs (referred to as an occurrence probability for brevity). In some embodiments, the occurrence probability may relate to at least one of an application scenario of the CT device, an equipment type of the CT device, an usage frequency of the CT device, an usage environment of the CT device, connection manners between the plurality of data sending units and the plurality of first communication links, connection manners between the plurality of data sending units and the at least one second communication link, a count of communication links that have one or more historical failures, a count of the one or more historical failures, or the like, or any combination thereof.

More second communication link(s) may be used, and/or the second communication link(s) may be arranged more densely if the occurrence probability has a great value. For example, the count and/or density of the second communication link(s) may be proportional to the occurrence probability.

In some embodiments, the occurrence probability may be large if the application scenario of the CT device is complex, the equipment type of the CT device is primary, the usage frequency of the CT device is high, the usage environment of the CT device is terrible, the efficiency of the connection manners between the plurality of data sending units and the plurality of first communication links is low, the efficiency of the connection manners between the plurality of data sending units and the second communication link(s) is low, the count communication links that has one or more historical failures is large, or the count of the one or more historical failures is large.

In some embodiments, historical usage data of a plurality of CT devices of the same type may be obtained, and the count of communication links that have one or more historical failures and the count of the one or more historical failures may be determined based on the historical usage data to determine the probability that a communication link failure occurs. In some embodiments, the count and/or the arrangement manner of the second communication link(s) may be determined based on the occurrence probability. For example, a plurality of ranges corresponding to different counts of the second communication link(s) may be determined, and the count of the second communication link(s) may be determined based on the occurrence probability. For example, four second communication links may be arranged when the occurrence probability is in a range of 20%-30%, and three second communication links may be arranged when the occurrence probability is in a range of 10%-20%.

In some embodiments, occurrence probabilities corresponding to different types of CT devices may be determined. The count and/or the arrangement manner of the second communication link(s) may be determined based on the occurrence probabilities corresponding to the different types of CT devices. For example, a CT device with a large occurrence probability may include more second communication links. In some embodiments, the count of the second communication link(s) may be determined based on the occurrence probabilities corresponding to the different types of CT devices, and the arrangement manner of the second communication link(s) may be determined based on the count of the second communication link(s). For example, if the count of the second communication link(s) is less than five, the second communication links may be arranged at positions close to two sides of the data processing board; if the count of the second communication link(s) is greater than five and less than ten, the second communication links may be arranged at intervals with the first communication links (e.g., three or more first communication links may be arranged between a pair of second communication links).

In some embodiments, occurrence probabilities corresponding to different application scenarios and/or usage environments of CT devices may be determined, and the count and/or the arrangement manner of the second communication link(s) may be determined based on the determined occurrence probabilities. In some embodiments, the count and/or the arrangement manner of the second communication link(s) may be determined based on the application scenario and/or the usage environment of the CT device. For example, since the maintenance cost of a CT device in remote areas is high, and the maintenance efficiency of the CT device in remote areas is low, more second communication links may be arranged for the CT device. As another example, if a count of usage is greater than a first threshold and/or a usage frequency of the CT device is greater than a second threshold, the occurrence probability of the CT device may be large, and more second communication links may be arranged for the CT device.

In some embodiments, the count and/or the arrangement manner of the second communication link(s) may be determined based on the connection manners between the data sending units and the data processing unit (i.e., the connection manners between the data sending units and the first communication links, and the connection manners between the data sending units and the second communication link(s)). For example, the data sending units may be connected to the data processing unit via cables. The second communication link(s) may be arranged at intervals with the first communication links due to a length restriction of the cable.

For example, one or more second communication links may be arranged beside each first communication link (e.g., as shown in FIG. 6), or a second communication link may be arranged every five first communication links. As another example, the data sending units may be communicatively connected to the data processing unit through the short distance non-contact communication mode. The second communication link may be arranged based on the signal coverage area. For example, if the signal coverage area is 10 mm, one or more second communication links may be arranged within a range of 10 mm from each first communication link.

In some embodiments, the count and/or the arrangement manner of the second communication link(s) may be determined based on the usage frequency of the CT device. For example, the greater the usage frequency, the greater the occurrence probability may be, and more second communication links may be arranged.

In some embodiments, the count and/or the arrangement manner of the second communication link(s) may be determined based on a combination of the one or more influencing factors mentioned above. For example, more second communication links may be arranged for a CT device having a high occurrence probability. Then, the probability that each first communication link has a communication link failure may be determined, and the second communication links may be arranged closer to one or more first communication links that have the probability greater than a threshold value.

In some embodiments, a probability that a communication link failure occurs may be determined based on a trained second machine learning model. A second machine learning model may include a neural network model, such as CNN, RNN, DNN, or the like.

An input of the second machine learning model may include related information (e.g., a quantity and a location) of the first communication links (e.g., an application scenario of the CT device, an equipment type of the CT device, an usage frequency of the CT device, an usage environment of the CT device, connection manners between the plurality of data sending units and the plurality of first communication links, connection manners between the plurality of data sending units and the at least one second communication link, a first communication link that has one or more historical failures, a count of the one or more historical failures, etc.). An output of the second machine learning model may include the probability that a communication link failure occurs.

The second machine learning model may be obtained based on second training samples with labels. For example, a second training sample may include related information (e.g., a quantity and a location) of sample first communication links. The training label of the second training sample may include a probability that the sample first communication links of the second training sample have a communication link failure. The plurality of second training samples with labels may be input into a second preliminary machine learning model. A second loss function may be determined based on the labels and a predicted result output by the second preliminary machine learning model. Parameters of the second preliminary machine learning model may be iteratively updated by gradient descent or other methods based on the second loss function. The training of the second machine learning model may be terminated when a preset condition is satisfied, and the trained second machine learning model may be obtained. The preset condition may include that the second loss function converges (e.g., having a value lower than a threshold), that a count of iterations reaches a threshold, or the like.

In some embodiments, different data processing boards of the data processing unit may be connected to the same count or different counts of second communication links. The arrangement manners of the second communication links that are connected to different data processing boards may be the same or different. For example, for a data processing board with a better connecting effect, the count of the second communication link(s) may be smaller, and a density of the arrangement manner of the second communication link(s) may be lower. Merely as an example, if a performance coefficient of a board 1 is $m_1$, a performance coefficient of a board 2 is $m_2$, and $m_1 > m_2$, a count of the second communication link(s) that is connected to the board 1 may be smaller, and a density of an arrangement manner of the second communication link(s) that is connected to the board 1 may be lower.

In some embodiments, an adjustment manner for adjusting the first communication link group to the second communication link group may be determined based on the types of the first communication links and the second communication link(s). For example, when the first communication links and the second communication link(s) are cables, the first communication link group may be adjusted to the second communication link group through manual operation. As another example, when the first communication links and the second communication link(s) are the short distance non-contact communication links, the data processing unit 220 may automatically adjust the first communication link group to the second communication link group.

In some embodiments, the plurality of first communication links may be configured to establish a plurality of communication connections between two data processing boards of the data processing unit 220, and the at least one second communication link is configured to replace at least one failed communication link when the plurality of first communication links include the at least one failed communication link. As shown in FIG. 5, the first communication link group may be configured to establish the communication connections between the A Board and the C board, or between the B Board and the C board, and the C board is communicatively connected to second communication link 573. In some embodiments, the first communication link group may be or the first communication link group may be configured to establish the communication connections between the C Board and the D Board, the D Board is communicatively connected to second communication link 575.

Figure 3:
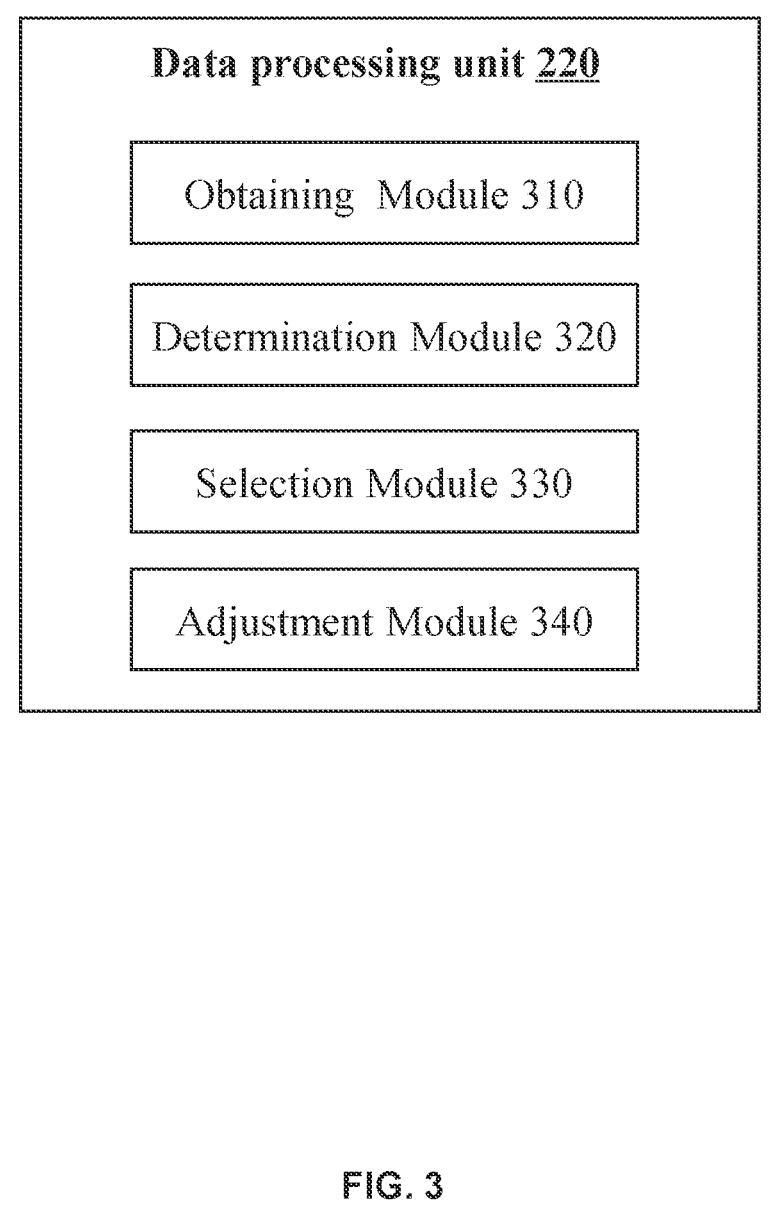

FIG. 3 is a block diagram illustrating an exemplary data processing unit according to some embodiments of the present disclosure. As shown in FIG. 3, the data processing unit 220 may include an obtaining module 310, a determination module 320, a selection module 330, and an adjustment module 340.

In some embodiments, the obtaining module 310 may be used to receive data sent by a plurality of data sending units through a first communication link group.

In some embodiments, the determination module 320 may be used to determine whether the first communication link group includes at least one failed communication link.

In some embodiments, the selection module 330 may be used to select at least one target communication link matching the failed communication link(s) from at least one second communication link.

In some embodiments, the adjustment module 340 may be used to adjust the first communication link group to a second communication link group for establishing communication connections between the data processing unit 220 and the data sending units.

More descriptions regarding the obtaining module 310, the determination module 320, the selection module 330, and the adjustment module 340 may be found elsewhere in the present disclosure. See, e.g., FIGS. 4 and 8 and relevant descriptions thereof.

Figure 4:
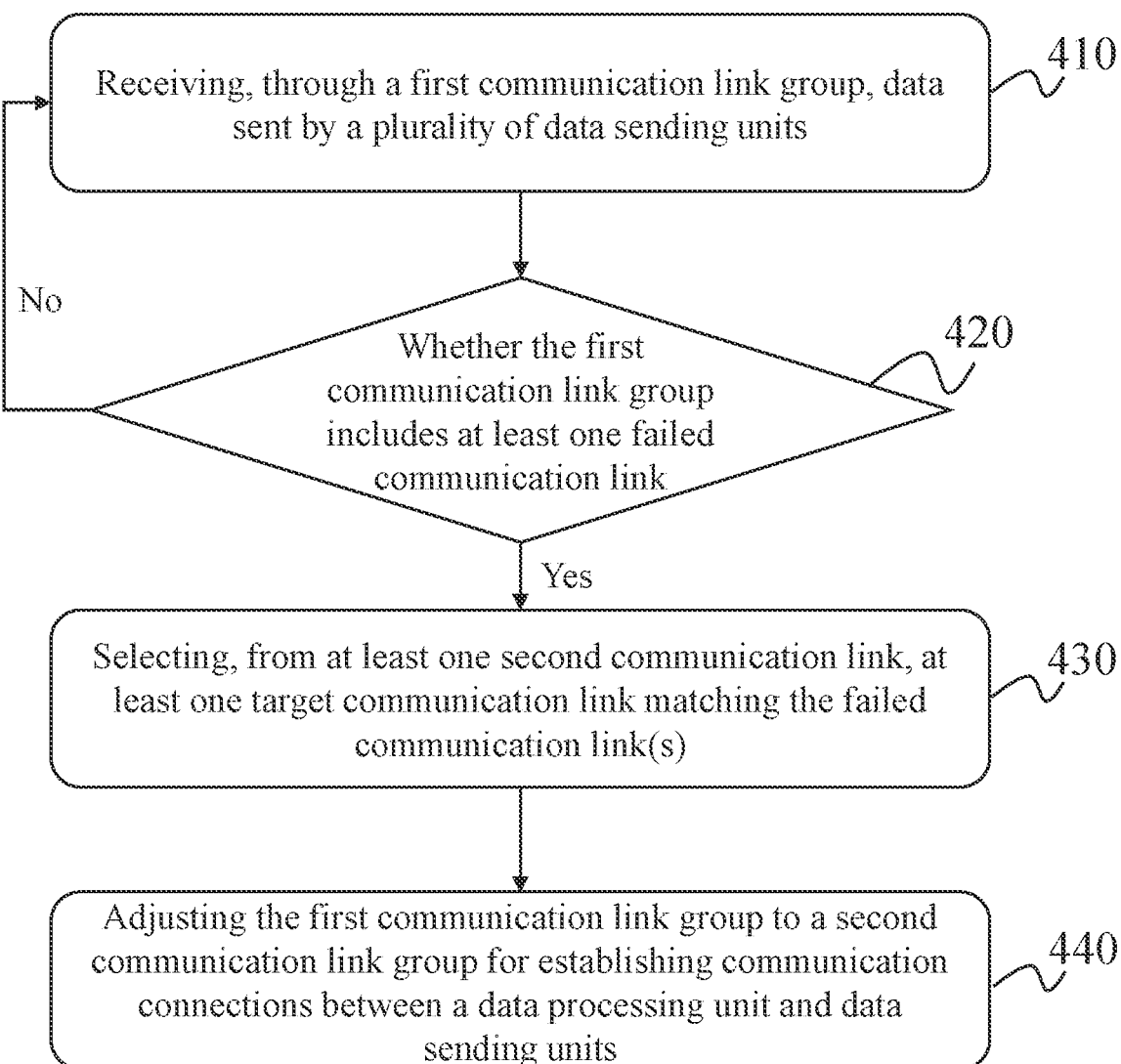
FIG. 4 is an exemplary flowchart illustrating an exemplary process for data transmission according to some embodiments of the present disclosure.

FIG. 4 is an exemplary flowchart illustrating an exemplary process for data transmission according to some embodiments of the present disclosure. In some embodiments, a process 400 for data transmission may be performed by a data transmission device, such as the data transmission device 160, the data transmission device 200. For example, the process 400 may be stored in a storage device (e.g., the storage device 150) in a form of programs or instructions. The process 400 may be performed when the data transmission device 200 (e.g., the data processing unit 220) executes the programs or the instructions. Operations of the illustrated process 400 presented below are intended to be illustrative. In some embodiments, the process 400 may be accomplished with one or more additional operations not described, and/or without one or more of operations discussed. Additionally, the order of operations of the process 400 illustrated in FIG. 4 and described below is not intended to be limiting.

In operation 410, data sent by a plurality of data sending units may be received through a first communication link group. In some embodiments, operation 410 may be performed by the obtaining module 310 of the data processing unit 220.

The first communication link group may include one or more first communication links for establishing the communication connections between the data processing unit (e.g., the data processing unit 220) and the data sending units (e.g., the data sending units 1-$n$ shown in FIG. 2), such as the first communication link 1, the first communication link 2, ..., and the first communication link n shown in FIG. 2. In some embodiments, the first communication links may include high-speed digital communication links. For example, the communication rate of a high-speed digital communication link may be 6 Gb/s or more than 6 Gb/s. In some embodiments, the first communication link group may include a plurality of first communication links arranged adjacent to each other and/or a plurality of first communication links arranged at intervals. For example, if no other communication links are located between a pair of first communication links, the pair of first communication links may be deemed as being arranged adjacent to each other. As another example, if one or more second communication links are located between a pair of first communication links, the pair of first communication links may be deemed as arranged at intervals.

In some embodiments, the data sending units may include a plurality of detector modules (e.g., a plurality of DBBs as shown in FIG. 5 to FIG. 7) of the CT device. Each of the plurality of data sending units may correspond to each of the plurality of detector modules.

In some embodiments, data sent by the data sending units through the first communication link group may include test data or scan data.

The test data may refer to data that is used to detect an occurrence of a communication link failure. For example, the data sending units may send test data packages to the data processing unit 220 through the first communication link group every specific time period (e.g., 3 s, 5 s, 10 s, 5 minutes, etc.) or in real time. In some embodiments, the test data packages sent by the data sending units may be received through the first communication link group before performing a CT scan, or after the CT device is turned on, or when the CT device is on standby, or in other processes.

The scan data may be obtained by scanning a target object. For example, the scan data sent by the data sending units may be received through the first communication link group in a process of a CT scan of the target object.

In some embodiments, the data processing unit 220 may send a connection request for establishing a connection to the data sending units through the first communication link group, and the data sending units may send a response result corresponding to the connection request through the first communication link group. The response result may be used to determine whether the first communication link group includes at least one failed communication link. In operation 420, whether the first communication link group includes at least one failed communication link may be determined. In some embodiments, operation 420 may be performed by the determination module 320 of the data processing unit 220.

In some embodiments, when the data received from the data sending units is empty (i.e., no data is sent by the data sending units through the first communication link group), the first communication link group may include the failed communication link(s). In some embodiments, when the data includes a missing part and/or the data includes errors, the first communication link group may include the failed communication link(s). In some embodiments, when the data sending units do not respond to the connection request sent by the data processing unit 220 or the connections between the data sending units and the data processing unit 220 fail to be established, the first communication link group may include the failed communication link(s).

In some embodiments, when the first communication link group includes the failed communication link(s), the data processing unit 220 may further determine the failed communication link(s) from the first communication links. For example, each of the first communication links may be communicatively connected to a data sending unit. If the data processing unit 220 cannot receive data sent by a data sending unit through a corresponding first communication link, or the received data includes a missing part and/or the received data includes errors, the first communication link may be determined as a failed communication link. For example, if the data processing unit 220 sends the connection request to a data sending unit through a corresponding first communication link, but fails to receive a response returned by the data sending unit in response to the connection request, the first communication link may be determined as a failed communication link.

In operation 430, at least one target communication link matching the failed communication link(s) may be selected from the second communication link(s). In some embodiments, operation 430 may be performed by the selection module 330 of the data processing unit 220.

A second communication link may refer to a communication link that is connected to the processing unit 220, but not connected to a data sending unit. In some embodiments, the second communication link may be a preset idle interface of the data processing unit 220, or an idle interface connected to the data processing unit 220 through a connector. For example, the data processing unit 220 may be an FPGA processor of a data processing board, one, two, or more connectors interconnected with the detector modules on the data processing board may be used as the second communication link(s).

More details about the first communication links and the second communication link(s) may refer to FIG. 2 and the related descriptions, which are not repeated herein.

In some embodiments, for each of the failed communication link(s), a target communication link matching the failed communication link may be selected from the second communication link(s). The target communication link matching a failed communication link may be a second communication link that is used to replace the failed communication link to communicate with the data sending device 210.

In some embodiments, when the first communication link group includes the failed communication link(s), at least one target communication link(s) matching the failed communication link(s) may be selected from the second communication link(s).

In some embodiments, for each of the failed communication link(s), a count of communication links located between the failed communication link and each of the second communication link(s) may be determined. A second communication link corresponding to a minimum count of communication links may be selected from the second communication link(s), and the selected second communication link may be determined as the target communication link corresponding to the failed communication link. For example, as shown in FIG. 2, it is assumed that the first communication link 2 for establishing the communication connection between the data processing unit 220 and the data sending unit 2 fails. Since the count of communication links between the first communication link 2 and the second communication link 1 is 1, the count of communication links between the first communication link 2 and the second communication link 2 is 0, and the count of communication links between the first communication link 2 and the second communication link 3 is more than 2, the second communication link 2 with the minimum count of communication links may be determined as the target communication link corresponding to the first communication link 2.

In some embodiments, two second communication links that are closest to the failed communication link may be determined respectively in a direction from the failed communication link to a first end of the data processing board and a direction from the failed communication link to a second end of the data processing board (e.g., a first end and a second end of the data processing unit 220 shown in FIG. 2). Counts of communication links located between the failed communication link and each of the two second communication links may be determined. A second communication link with a minimum count of communication links may be selected from the two second communication links, and the selected second communication link may be determined as the target communication link corresponding to the failed communication link. Merely as an example, as shown in FIG. 7, the communication links that are connected to the DBBs may be denoted as first communication links, other idle communication links may be denoted as second communication links. In the A board, if a first communication link 750 marked with "x" fails, a second communication link 710 that is closest to the first communication link 750 in a direction from the right side to the left side of the board A, and a second communication link 720 that is closest to the first communication link 750 in a direction from the left side to the right side of the A Board may be determined. Because the count of communication links between the second communication link 710 and the first communication link 750 is smaller than the count of communication link between the second communication link 720 and the first communication link 750, the second communication link 710 may be determined as the target communication link corresponding to the first communication link 750.

In some embodiments, a data processing device may include at least two data processing boards. The second communication link(s) may be communicatively connected to at least one of the data processing boards. More details may refer to FIG. 2 and the related descriptions, which are not repeated herein. In some embodiments, for each of the failed communication link(s), at least one candidate communication link connected to a same data processing board with the failed communication link may be selected from the second communication link(s). A target communication link matching the failed communication link may be determined based on the candidate communication link(s). In some embodiments, for each of the failed communication link(s), the candidate communication link with a minimum count of communication links that are located between the failed communication link and the candidate communication link may be determined as the target communication link corresponding to the failed communication link. As shown in FIG. 5, when a first communication link that is connected to the A Board fails, second communication link(s) that are connected to the A Board may be determined as candidate communication link(s), and the second communication link that is closest to the first communication link may be selected from the candidate communication link(s) as the corresponding target communication link.

In some embodiments, if a failed communication link is connected to a data processing board of the data processing unit 220, a target communication link corresponding to the failed communication link may be selected from the failed communication link(s) that is connected to other data processing boards. For example, as shown in FIG. 5, if a first communication link that is connected to the B Board failed, second communication link(s) that are connected to the A Board may be determined as candidate communication link(s), and the second communication link that is closest to the first communication link may be selected from the candidate communication link as the corresponding target communication link.

In some embodiments, a second communication link that is closer to an edge of the data processing board may be obtained, and the second communication link that is closer to the edge of the data processing board may be determined as the target communication link corresponding to a failed communication link. Merely as an example, as shown in FIG. 5, the communication links that are connected to the DBBs may be denoted as the first communication links, other idle communication links may be denoted as the second communication links. A second communication link 510 and a second communication link 520 may be arranged at the rightmost end of the A board and the leftmost end of the B board, respectively. When a first communication link 530 and a first communication link 540 marked with "x" fails, the second communication link 510 may be selected as the target communication link corresponding to the first communication link 530, and the second communication link 520 may be selected as the target communication link corresponding to the first communication link 540.

In some embodiments, for a failed communication link, one or more second communication links that are connected to the same data processing board of the data processing unit 220 and adjacent to the failed communication link may be determined, and the target communication link corresponding to the failed communication link may be selected from the adjacent second communication link(s). Merely as an example, as shown in FIG. 6, the communication links that are connected to the DBBs may be denoted as the first communication links, other idle communication links may be denoted as the second communication links. In the board A, when the first communication link 610 marked with "x" fails, a second communication link 620 and a second communication link 630 that are adjacent to the failed communication link may be determined, and one of the second communication links 620 and 630 may be selected as the target communication link corresponding to the failed communication link 610.

In operation 440, a first communication link group may be adjusted to a second communication link group for establishing the communication connections between the data processing unit 220 and the data sending units. In some embodiments, operation 440 may be performed by the adjustment module 340 of the data processing unit 220.

The second communication link group may include the target communication link(s) and one or more first communication links that are not failed.

In some embodiments, for each of the failed communication link(s), an identification of the target communication link matching the failed communication link may be obtained, and a communication connection between the target communication link and the data sending unit that is communicatively connected to the failed communication link may be established based on the identification of the target communication link. An identification of a communication link may be a channel ID.

In some embodiments, for each of the failed communication link(s), an identification of the target communication link matching the failed communication link may be obtained. A plurality of target data sending units may be determined based on the identification of the target communication link. The target data sending units may be communicatively connected to the failed communication link and one or more first communication links that are located between the failed communication link and the target communication link. The communication links that are communicatively connected to the target data sending units may be sequentially adjusted based on a direction from the target communication link to the failed communication link until the target data sending unit corresponding to the failed communication link establishes a communication connection with a normal communication link.

Merely as an example, as shown in FIG. 7, a DBB a is connected to a first communication link 770, and a DBB b is connected to a first communication link 780. If the first communication link 770 fails, a second communication link 790 may be determined as the target communication link corresponding to the first communication link 770. The DBB a corresponding to the failed communication link 770 and the DBB b corresponding to the first communication link 780 between the failed communication link 770 and the target communication link 790 may be determined as target DBBs. The communication links connecting to the DBBs a and b may be sequentially adjusted from the direction from the target communication link 790 to the failed communication link 770. For example, the DBB b may be adjusted to establish a communication connection to the target communication link 790, and the DBB a may be adjusted to establish a communication connection to the first communication link 780. In this way, both the DBBs a and b may be connected to normal communication links.

In some embodiments, a user (e.g., an equipment maintenance personnel, an operator) may adjust the first communication link group to the second communication link group for establishing the communication connections between the data processing unit 220 and the data sending units based on the identification of the target communication link(s). In some embodiments, the first communication link group may be automatically adjusted to the second communication link group. For example, the data processing unit 220 may determine a target data sending unit corresponding to a failed communication link based on an identification of the failed communication link. The data processing unit 220 may further determine a connection key of the target communication link based on the identification of the target communication link. Then, the data processing unit 220 may broadcast the connection key to the target data sending unit, so that the target data sending unit may be communicatively connected to the target communication link through the connection key.

In some embodiments, data sent by the data sending units may be received through the second communication link group to facilitate subsequent processing. More details may refer to FIG. 8 and the related descriptions, which are not repeated herein.

It should be noted that the descriptions of the process 400 may be only for examples and illustrations and do not limit the scope of the present disclosure. For those skilled in the art, various modifications and changes may be made to the process 400 under the guidance of the present disclosure. However, the amendments and changes may be still within the scope of the present disclosure.

FIGS. 5-7 are schematic diagrams illustrating exemplary data transmission devices according to some embodiments of the present disclosure.

In FIGS. 5-7, the data processing unit includes two data processing boards, namely the A board and B board. The two boards may be respectively connected with a plurality of detector modules (DBB) to obtain scan data, and configured to perform a preprocessing operation (e.g., rearrangement, merging) on the scan data, and transmit the preprocessed scan data to the C board. The C board may further process the preprocessed scan data to obtain processed scan data, and transmit the processed scan data to the D board (e.g., a data processing board of the processing device 140. Thus, the data transmission device may complete the data transmission process from the detector to the data processing unit.

In FIG. 5, a second communication link 510 is closest to the right end of the Aboard, and a second communication link 520 is closest to the left end of the B board. Then, in the A board, if the first communication link 530 fails, the second communication link 510 may be used as an alternative communication link (i.e., the target communication link) to replace the failed communication link 530. In the B board, if the first communication link 540 fails, the second communication link 520 may be used as an alternative communication link to replace the failed communication link 540. Thus, it may ensure that the scan data sent by the detector may be normally transmitted to the A board and the B board. Then, the failed communication link 530 and the first communication links between the failed communication link 530 and the second communication link 510 may be translated in a direction from the left to the right to the second communication link 510 and the first communication links between the failed communication link 530 and the second communication link 510. For example, in the A board, the right-most DBB 550 may be adjusted to establish a connection to the second communication link 510, and the DBB 560 adjacent to the right-most DBB may be then adjusted to establish a connection to the first communication link 570 adjacent to the second communication link 510.

In some embodiments, an identification of the second communication link 510 and/or an identification of the second communication link 520 may be obtained, and the identification of the second communication link 510 and/or the identification of the second communication link 520 may be determined as the identification(s) of the target communication link(s) that match the failed communication link(s).

Specifically, the second communication links 510 and 520 may be located at both ends of the data processing unit, and the data processing unit 220 may determine their identifications based on their respective locations.

In this embodiment, by disposing the second communication link(s) closer to an edge of the data processing unit than the first communication links, the second communication link(s) may be quickly and conveniently found when searching for the second communication link(s).

In FIG. 6, the first communication links and the second communication links connected to the A board may be disposed at intervals, and the first communication links and the second communication links connected to the B board may be also disposed at intervals. Then, in the A board, when the first communication link 610 marked with an "x" mark fails, any one of the two second communication links 620 and 630 adjacent to the failed communication link 610 may be selected as the target communication link of the failed communication link 610. In the B board, when the first communication link 640 marked with an "x" mark fails, any one of the two second communication links 650 and 660 adjacent to the failed communication link 640 may be selected as the target communication link of the failed communication link 640, so as to ensure that the scan data sent by the detector may be normally transmitted to the A board and the B board. Then, the DBB connecting to the failed communication link 610 may be adjusted to establish a communication connection with the second communication link 620 or the second communication link 630, and the DBB connecting to the failed communication link 640 may be adjusted to establish a communication connection with the second communication link 650 or the second communication link 660.

By disposing the first communication links and the second communication links at intervals, a second communication link nearby a failed communication link may be determined as the corresponding target communication link, and the workload of the communication link adjustment can be reduced.

In FIG. 7, six first communication links are arraigned between the second communication link 710 and the second communication link 720 in the A board, and eight first communication links are arraigned between the second communication link 730 and the second communication link 740 in the B board. Then, in the A board, when the first communication link 750 marked with an "x" mark fails, the second communication link 710 with the closest distance to the failed communication link 750 may be determined as the target communication link of the failed communication link 750. In the B board, when the first communication link 760 marked with an "x" mark fails, the second communication link 740 with the closest distance to the failed communication link 760 may be determined as the target communication link of the failed communication link 760. Then, the communication links connected to the DBBs c and d may be translated in a direction from the failed communication link 750 to the target communication link 710. For example, the DBB c may be adjusted to be connected to the target communication link 710, and the DBB d may be may be adjusted to be connected to the first communication link 715. In such cases, the total translation steps corresponding to the failed communication link 750 may be two steps, which include one translation step for translating the communication link corresponding to the DBB c and one translation step for translating the communication link corresponding to the DBB d. In the B board, the communication links connected to the DBBs e, f, and g may be translated in a direction from the failed communication link 760 to the target communication link 740. For example, the DBB e may be adjusted to be connected to the target communication link 740, the DBB f may be adjusted to be connected to the first communication link 765, and the DBB g may be adjusted to be connected to the first communication link 763. In such cases, the total translation steps corresponding to the failed communication link 760 may be three steps, which include one translation step for translating the communication link corresponding to the DBB e, one translation step for translating the communication link corresponding to the DBB f and one translation step for translating the communication link corresponding to the DBB g.

FIG. 8 is an exemplary flowchart illustrating an exemplary process for data transmission according to some embodiments of the present disclosure.

In some embodiments, the scan data transmission process 800 may be performed by a data transmission device, such as the data transmission device 160 and the data transmission device 200. For example, the scan data transmission process 800 may be stored in a storage device (E. G., the storage device 150) in the form of a program or an instruction, and the scan data transmission process 800 may be implemented when the data transmission device 200 (e.g., the data processing unit 220) executes the program or the instruction. Operations of the illustrated process 800 presented below are intended to be illustrative. In some embodiments, the process 800 may be accomplished with one or more additional operations not described, and/or without one or more of operations discussed. Additionally, the order of operations of the process 800 illustrated in FIG. 8 and described below is not intended to be limiting.

In operation 810, data sent by detector modules may be received through a first communication link group. In some embodiments, operation 810 may be performed by the obtaining module 310.

In some embodiments, a test data packet sent by the detector modules may be received through the first communication link group before a CT device performs a scan, after the CT device is turned on, or when the CT device is on standby. In some embodiments, scan data sent by the detector modules may be received through the first communication link group during a scanning process of the CT device. In some embodiments, the data processing unit may send a connection request to establish a connection to the detector modules through the first communication link group, and the detector modules may send a response result to the connection request through the first communication link group. The response result may be used to determine whether the first communication link group includes at least one failed communication link. In some embodiments, operation 810 may be performed in a similar manner as operation 410, and the descriptions thereof are not repeated here.

In operation 820, whether the first communication link group includes at least one failed communication link may be determined. In some embodiments, operation 820 may be performed by the determination module 320.

In some embodiments, when the data is empty (i.e., no data is sent by the data sending units through the first communication link group), it may be determined that the first communication link group includes the failed communication link(s). In some embodiments, when the data includes a missing part and/or the data includes errors, it may be determined that the first communication link group includes the failed communication link(s). In some embodiments, when the detector module does not respond to the connection request sent by the data processing unit or the connection between the detector module and the data processing unit fails to be established, it may be determined that the first communication link group includes the failed communication link(s). In some embodiments, operation 820 may be performed in a similar manner as operation 420, and the descriptions thereof are not repeated here.

In operation 830, a target communication link matching the failed communication link(s) may be selected from the second communication link(s). In some embodiments, operation 830 may be performed by the selection module 330.

In some embodiments, the target communication link(s) matching the failed communication link(s) may be selected from the second communication link(s) in response to determining that the first communication link group includes the failed communication link(s). In some embodiments, operation 830 may be performed in a similar manner as operation 430, and the descriptions thereof are not repeated here.

In operation 840, the first communication link group may be adjusted to a second communication link group for establishing the communication connections between the data processing unit and the detector modules. In some embodiments, operation 840 may be performed by the adjustment module 340.

In some embodiments, based on the identification(s) of the target communication link(s), the first communication link group may be adjusted to the second communication link group. In some embodiments, the first communication link group may include the fault communication link(s) and normal first communication link(s), and the second communication link may include the target communication link(s) and the normal first communication link(s). In some embodiments, operation 840 may be performed in a similar manner as operation 440, and the descriptions thereof are not repeated here.

After detecting the failed communication link(s) and adjusting the first communication link group to the second communication link group, the data processing unit may receive and process scan data sent by the detector modules through the second communication link group. For example, operation 850 and operation 860 may be performed.

In operation 850, the scan data sent by the detector modules may be received through the second communication link group. In some embodiments, operation 850 may be performed by the obtaining module 310.

Figure 9:
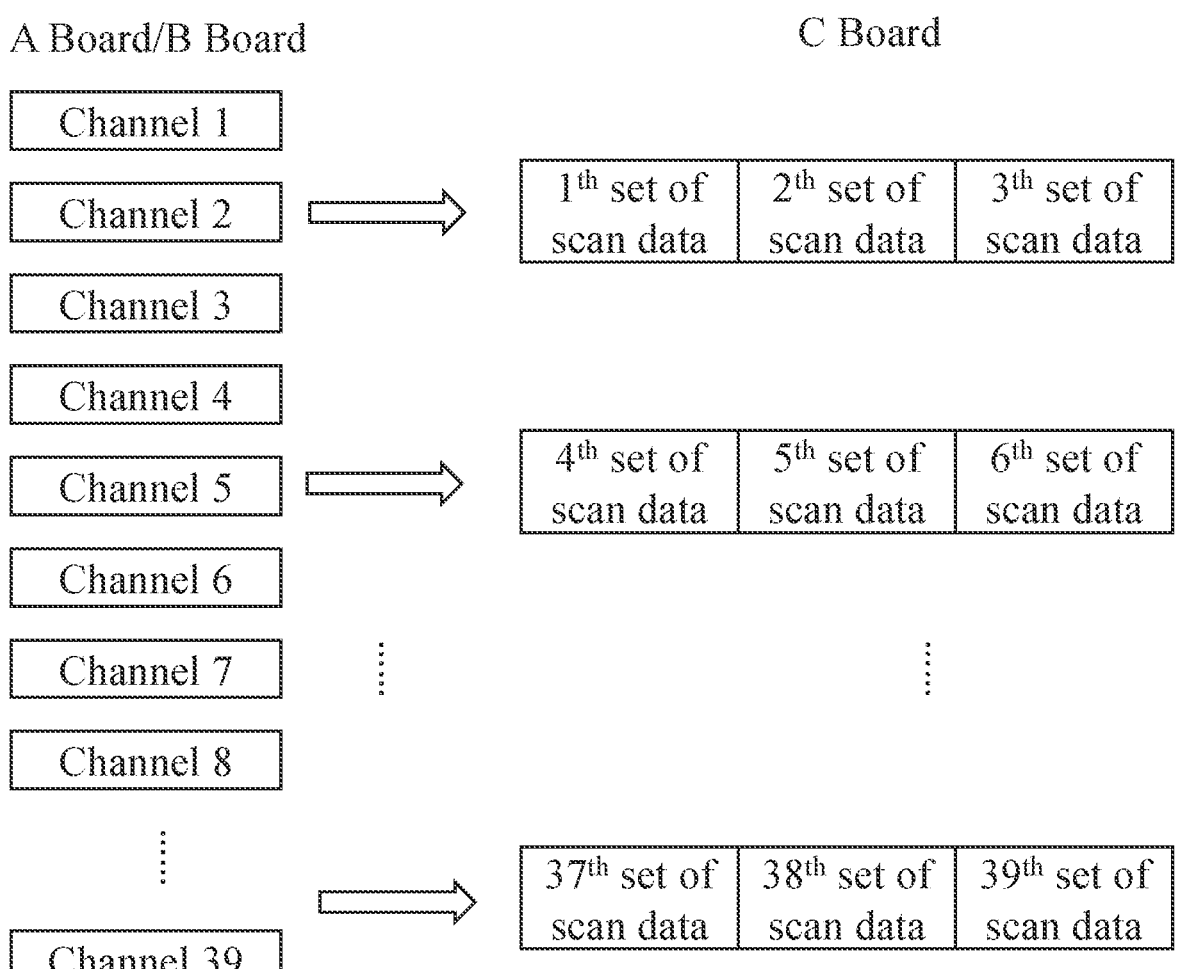
FIG. 9 is a schematic diagram illustrating an exemplary application scenario when data transmission is normal according to some embodiments of the present disclosure.

In some embodiments, a communication link (i.e., each communication link in the second communication link group) for establishing the communication connection between each detector module and the data processing unit may be defined as a data transmission channel. For example, as shown in FIG. 9, if the CT device includes 39 detector modules (i.e., a detector module 1, a detector module 2, . . . , and a detector module 39), a channel number of each communication link may be determined according to an identification of the detector module connected to each communication link. For example, the communication link connected to the detector module 1 may be defined as a channel 1, the communication link connected to the detector module 2 may be defined as a channel 2, . . . , and the communication link connected to the detector module 39 may be defined as a channel 39. In some embodiments, the scan data received through the second communication link group may include a plurality of sets of scan data each of which is received from one channel. For example, the scan data may include the first set of scan data received from the channel 1, the second set of scan data received from the channel 2, . . . , and the 39th set of scan data received from the channel 39.

In operation 860, data processing may be performed on the scan data and the processed scan data may be sent to an image reconstruction module. In some embodiments, operation 860 may be performed by the data processing unit 220.

In some embodiments, the scan data received through the second communication link group may include the sets of scan data received from the channels, and the data processing may include rearranging and/or merging the sets of scan data. For example, rearrangement may include sorting the sets of scan data according to the number of detector modules corresponding to the sets of scan data. Merging may include merging multiple sets of scan data collected by a plurality of specific detector modules.

In some embodiments, the received sets of scan data may be processed according to a ranking result of the sets of scan data to obtain the processed scan data. The ranking result may reflect a corresponding relationship between the sets of scan data and the data transmission channels (or the detector modules). For example, it is assumed that the $m^{th}$ set of scan data is received from a channel x (collected by a detector module x), and the $n^{th}$ set of scan data is received from a channel y (collected by a detector module y). If x is smaller than y, the $m^{th}$ set of scan data may be ranked before the $n^{th}$ set of scan data in the ranking result.

In some embodiments, the corresponding relationship (i.e., a connection relationship) between each communication link in the second communication link group and the detector modules may be obtained, and the ranking result of the sets of scan data may be determined according to the corresponding relationship. For example, if a first communication link 1 is connected to the detector module 1 and a second communication link 2 is connected to the detector module 39, the set of scan data received through the first communication link 1 may be ranked first in the ranking result, and the set of scan data received through the second communication link 2 may be ranked $39^{th}$ in the ranking result.

In some embodiments, the received sets of scan data may be rearranged and merged according to the ranking results to obtain the processed scan data.

Figure 10:
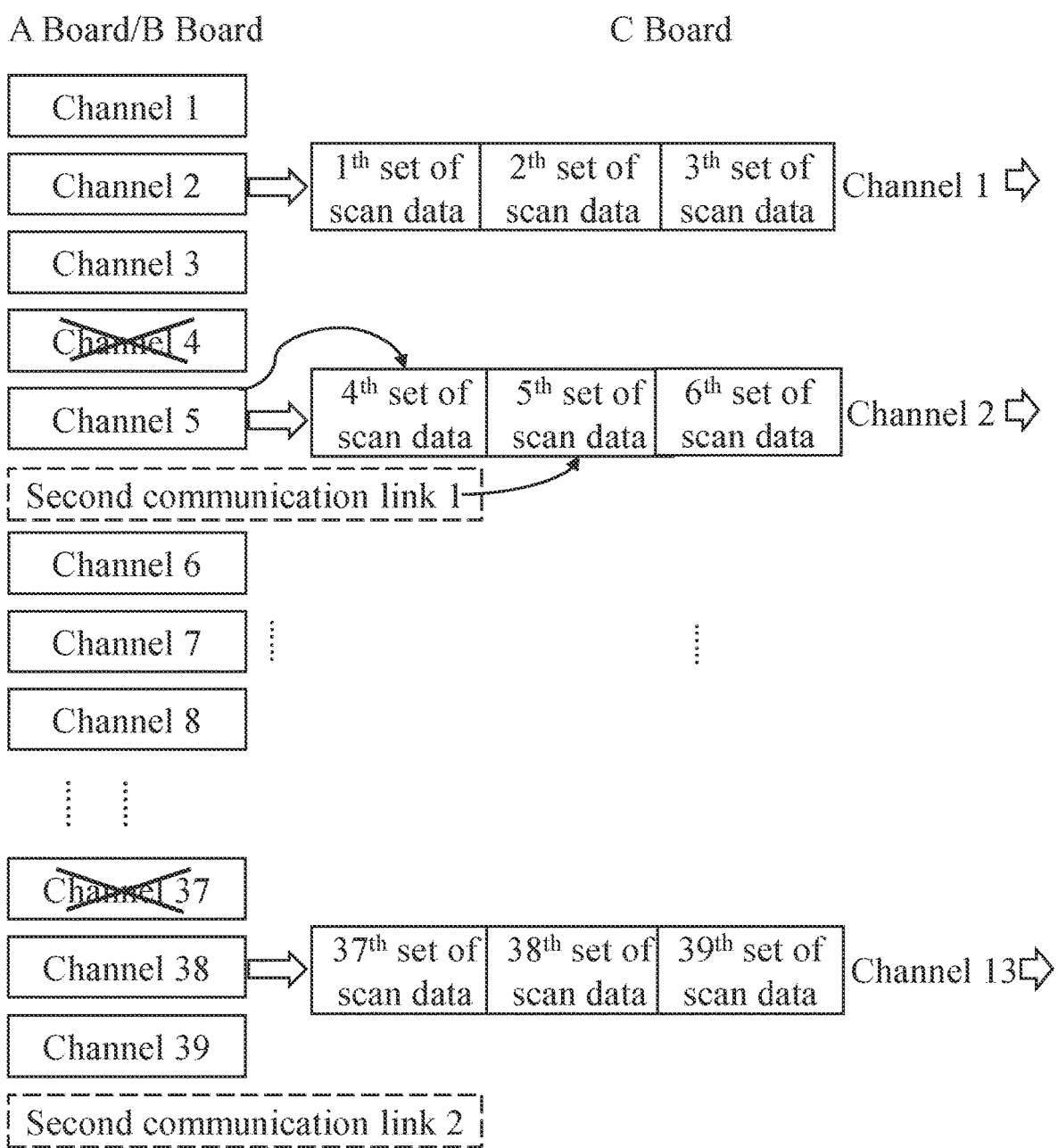
FIG. 10 is a schematic diagram illustrating an exemplary application scenario when data transmission is abnormal according to some embodiments of the present disclosure.

As an example only, as shown in FIG. 10, a second communication link 1 is disposed between a first communication link 5 corresponding to a channel 5 and a first communication link 6 corresponding to a channel 6. When a first communication link 4 corresponding to a channel 4 fails, the detector module 5 may establish a communication connection with the second communication link 1, and the detector module 4 may establish a communication connection with the first communication link 5 (i.e., the first communication link originally corresponding to the channel 5). That is, the second communication link 1 may be used as the channel 5 connected to the detector module 5, and the first communication link 5 may be used as the channel 4 connected to the detector module 4.

Then, after receiving the sets of scan data sent from the detector modules, the A board or the B board may rearrange the sets of scan data according to the corresponding relationship between the communication links and the detector modules. For example, as shown in FIG. 10, the fifth set of scan data received through the second communication link 1 (i.e., the channel 5) is ranked before the fourth set of scan data received through the first communication link 5 (i.e., the channel 4). Through data rearrangement, the sets of scan data may be arranged according to the serial number of the detector modules corresponding to the sets of scan data for subsequent processing. In some embodiments, the sorted sets of scan data may be merged. For example, as shown in FIG. 10, the first, second, and third sets of scan data may be merged into one set of scan data, . . . , the $37^{th}$ to $39^{th}$ sets of scan data may be merged into one set of scan data, and therefore, 13 sets of scan data may be generated.

In some embodiments, the data processing performed on the scan data may also include data projection, data filtering, data sorting, data modification, curve fitting, etc., which are not limited in the present disclosure.

In some embodiments, the processed scan data may be sent to the image reconstruction module, and image reconstruction may be performed on the processed scan data by the image reconstruction module to obtain a medical image. In some embodiments, the reconstructed medical image may include a 2D image, a 3D image, a 4D image, etc., or any combination thereof. In some embodiments, the image reconstruction module may perform the image reconstruction according to a reconstruction algorithm. For example, the reconstruction algorithm may include an iterative reconstruction algorithm (E. G., a statistical reconstruction algorithm), a Fourier slice theorem algorithm, a filtered back projection (FBP) algorithm, a fan beam reconstruction algorithm, an analytical reconstruction algorithm, etc., or any combination thereof.

In some embodiments of the present disclosure, by determining whether there is a failed communication link and receiving the scan data sent by the detector modules by replacing the communication link group, the communication link failure may be quickly repaired, and the adverse effects caused by the failed communication link may be reduced, and the overall transmission efficiency of the scan data may be improved.

It should be understood that the operations shown in FIG. 4 and FIG. 8 can be executed in other sequences. Moreover, an operation in FIG. 4 and FIG. 8 may include multiple steps or multiple phases. These steps or phases are not necessarily executed at the same time but can be executed at different times. The these steps or phases may not necessarily be performed sequentially but can be executed in turn or alternatively at the same time with other steps or phases in other operations.

Figure 12:
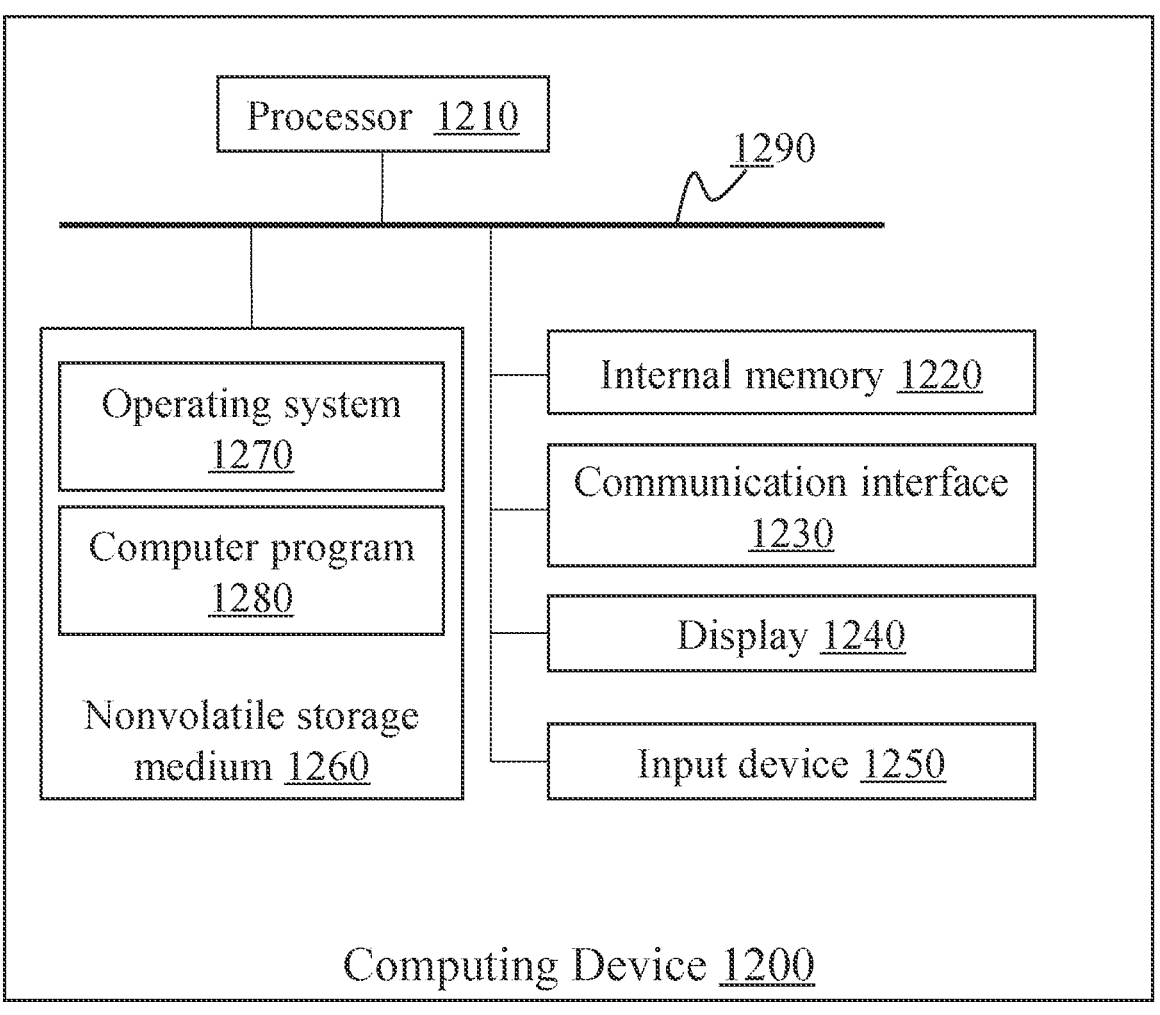
FIG. 12 is a schematic diagram illustrating exemplary hardware and/or software of a computing device according to some embodiments of the present disclosure.

FIG. 12 is a schematic diagram illustrating exemplary hardware and/or software of a computing device according to some embodiments of the present disclosure.

In some embodiments, one or more components of the data transmission system 100 may be implemented through the computing device 1200. For example, the data processing unit in the data transmission device 160, the processing device 140, and/or the terminal 130 may be implemented by the computing device 1200.

As shown in FIG. 12, in some embodiments, the computing device 1200 may include components connected to a system bus 1290, including a processor 1210, a memory, a communication interface 1230, a display 1240, and an input device 1250.

The processor 1210 may have computing and control capabilities. In some embodiments, the processor 1210 may include a microcontroller, a microprocessor, a reduced instruction set computer (RISC), an application specific integrated circuit (ASIC), an application specific instruction set processor (ASIP), a central processing unit (CPU), a graphics processing unit (GPU), a physical processing unit (PPU), a microcontroller unit, a digital signal processor (DSP), a field programmable gate array (FPGA), an advanced RISC machine (ARM), a programmable logic device and any circuit and processor capable of performing one or more functions, etc., or any combination thereof. For illustration only, the computing device 1200 in FIG. 12 describes only one processor, but it should be noted that the computing device 1200 in the present disclosure may also include a plurality of processors.

In some embodiments, the memory of the computing device 1200 may include a nonvolatile storage medium 1260 and an internal memory 1220. The nonvolatile storage medium 1260 may store an operating system 1270 and a computer program 1280. The internal memory 1220 may provide an environment for an operation of the operating system 1270 and the computer program 1280 in the non-volatile storage medium 1260. The computer program 1280 is executed by the processor 1210 to implement the method for data transmission disclosed in the present disclosure.

The communication interface 1230 may be configured to communicate with an external terminal (e.g., the scanning device 110, the terminal 130) through a network connection. The connection may be a wired connection, a wireless connection, or a combination of the two, and the wireless mode can be realized through WiFi, operator network, NFC (near field communication), or other technologies. In some embodiments, the communication interface 1230 may be a standardized port, such as RS232, RS485, etc. In some embodiments, the network interface 1230 may be a specially designed port. For example, the communication interface 1230 may be designed according to Digital Imaging and Communication in Medicine (DICOM).

The display 1240 and the input device 1250 may be configured to input or output signals, data, or information. In some embodiments, the display 1240 and the input device 1250 may enable a user to communicate with components in the data transmission system 100, such as the scanning device 110. Exemplary displays 1240 may include a liquid crystal display (LCD), an electronic ink display, a light emitting diode (LED) based display, a flat panel display, a curved surface display, a television device, a cathode ray tube (CRT), etc., or any combination thereof. Exemplary input devices 1250 may include a touch layer covered on a display, a key, a trackball, or a trackpad disposed on a housing of the computing device, an external keyboard, an external trackpad, or an external mouse, etc.

In some embodiments, the bus 1290 may include a data bus, an address bus, a control bus, an expansion bus, and a local bus. In some embodiments, the bus 1290 may include an accelerated graphics port (AGP) or other graphics bus, an extended industry standard architecture (EISA) bus, a front side bus (FSB), a hyper transport (HT) interconnection, an industry standard architecture (ISA) bus, an Infiniband interconnection, a Low pin count (LPC) bus, a memory bus, a micro channel architecture (MCA) bus, a peripheral component interconnect (PCI) bus, a PCI Express (PCI-X) bus, a serial advanced technology attachment (SATA) bus, a video electronics standards association local bus (VLB), etc., or any combination thereof. In some embodiments, bus 1290 may include one or more buses. Although specific buses are described and shown in the embodiments of the present disclosure, the present disclosure may consider any suitable bus or interconnection.

In some embodiments, the computing device 1200 may be a server, a personal computer, a personal digital assistant, other terminal devices, such as tablets, mobile phones, etc., or a cloud or a remote server. The embodiments of the present disclosure do not limit the specific form of the computing device.

Those skilled in the art can understand that the structure shown in FIG. 12 is only a block diagram of some structures related to the scheme of the present disclosure, and does not constitute a limitation of the computing device applied to the structure shown in FIG. 12 in the scheme of the present disclosure. The specific computing device may include more or fewer components than the computing device shown in the figure, or combine some components, or have different component arrangements.

Figure 13:
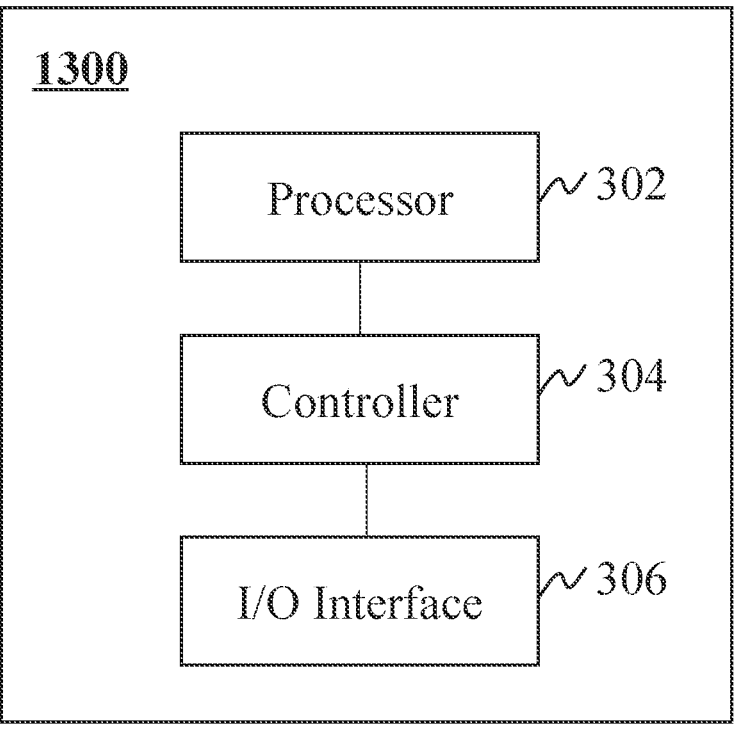
FIG. 13 is a schematic diagram illustrating exemplary hardware and/or software of another computing device according to some embodiments of the present disclosure.

FIG. 13 is a schematic diagram illustrating exemplary hardware and/or software of another computing device according to some embodiments of present disclosure.

In some embodiments, one or more components in the data transmission system 100 may be implemented by a computing device 1300. For example, the data processing unit in the data transmission device 160, the processing device 140, and/or the terminal 130 may be implemented by the computing device 1300. As shown in FIG. 13, the computing device 1300 may include a processor 302, a controller 304, and an I/O interface 306.

The processor 302 may be configured to select the target communication link(s) matching the failed communication link(s) from the second communication link(s) in response to determining that the first communication link group includes the failed communication link(s). The first communication link group may include the first communication links. The data processing unit may be communicatively connected with the first communication links and the second communication link(s).

The controller 304 may be configured to adjust the first communication link group to the second communication link group for establishing the communication connections between the data processing unit and the data sending units, and the second communication link group may include the target communication link(s). In some embodiments, the controller 304 may be configured to adjust the first communication link group to the second communication link group according to the identification of the target communication link(s).

The I/O interface 306 may be configured to receive the scan data sent by the data sending units through the second communication link group. The scan data may be processed and combined to obtain a reconstructed image from the CT device by performing image reconstruction.

In some embodiments, the computing device 1300 may be used in data transmission. For example, the computing device 1300 may be used in the transmission of CT scan data. If the first communication link group for establishing the communication connections between the data processing unit and the data sending units in the CT device includes the failed communication link(s), the target communication link(s) matching the failed communication link may be obtained. According to the identification of the target communication link(s), the target communication link(s) may be configured to replace the failed communication link(s), so as to adjust the communication links between the data processing unit and the data sending unit to establish normal communication connection to ensure data transmission. The device may quickly repair the communication link failure, reduce the adverse effects caused by the failed communication link(s), and improve the overall transmission efficiency of the scan data from the CT device.

In some embodiments, each module in the above computing device 1300 may be implemented in whole or in part by software, hardware, and combinations thereof. The above modules may be embedded in or independent of the processor in the computing device in the form of hardware, or stored in the memory in the computing device in the form of software, so that the processor can call and execute the corresponding operations of the above module.

The possible beneficial effects of some embodiments of the present disclosure include, but are not limited to: (1) The at least one second communication link is disposed on the data processing board as alternate communication link(s), and when a first communication link establishing a connection between the data processing unit and a data sending unit (e.g., a detector module) fails, a target communication link matching the failed communication link may be automatically determined. A first communication link group may be adjusted to a second communication link group for establishing the communication connections between the data processing unit and the data sending units (e.g., a plurality of detector modules) according to the identification of the target communication link(s). In this way, the communication link failure can be repaired, and the CT device may be restored to normal from the shutdown state in a timely and effective manner. In addition, the reliability of the data transmission and the use efficiency of the CT device may be improved; (2) In some embodiment, there is no need to add chips or circuits to the original data transmission device (e.g., the data processing unit), because the original data transmission device may include one or more redundant interfaces that can be used as the second communication link(s), or only several connectors are needed to provide the second communication links, and the equipment cost is low; (3) In some embodiment, a short distance non-contact high-speed wireless transmission mode is adopted, and the communication rate of the short distance non-contact high-speed wireless transmission mode is 6 GB/s or more than 6 Gb/s. When a first communication link of a specific detector module fails, through wireless automatic adaptation and connection establishment, a target communication link can be identified automatically to replace the failed communication link and transmit scan data of the specific detector module without using other connectors or human intervention. The device maintenance cost is low and the use efficiency is high. (4) In some embodiments, the second communication link(s) may be arranged at specific positions (e.g., near the end of the data processing unit, at intervals with the first communication links), so that the adjustment from the first communication link group to the second communication link group can be performed with an improved efficiency. It should be noted that different embodiments may produce different beneficial effects. In different embodiments, the possible beneficial effects can be any one or a combination of the above, or any other possible beneficial effects.

The basic concepts have been described above, apparently, in detail, as will be described above, and do not constitute a limitation of the present disclosure. Although there is no clear explanation here, those skilled in the art may make various modifications, improvements, and corrections for the present disclosure. This type of modification, improvement, and corrections are recommended in the present disclosure, so this class is corrected, improved, and the amendment remains in the spirit and scope of the exemplary embodiment of the present disclosure. Meanwhile, the present disclosure uses specific words to describe embodiments of the present specification. As "one embodiment", "an embodiment", and/or "some embodiments" means a certain feature, structure, or characteristic of at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Further, certain features, structures, or features of one or more embodiments of the present disclosure may be combined.

Moreover, unless otherwise specified in the claims, the sequence of the present disclosure, the order of the sequence of the present disclosure, the use of digital letters, or other names are not used to define the order of the present disclosure processes and methods. Although some embodiments of the invention currently considered useful have been discussed through various examples in the above disclosure, it should be understood that such details are only for the purpose of illustration, and the additional claims are not limited to the disclosed embodiments. On the contrary, the claims are intended to cover all amendments and equivalent combinations in line with the essence and scope of the embodiments of the specification. For example, although the implementation of various components described above may be embodied in a hardware device, it may also be implemented as a software-only solution, e.g., an installation on an existing server or mobile device.

Similarly, it should be noted that in order to simplify the expression disclosed in the present disclosure and help the understanding of one or more invention embodiments, in the previous description of the embodiments of the present disclosure, a variety of features are sometimes combined into one embodiment, drawings or description thereof. However, the present disclosure method does not mean that the features needed in the spectrum ratio of this disclosure ratio are more characteristic. Rather, claimed subject matter may lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially". Unless otherwise stated, "about," "approximate," or "substantially" may indicate ±20% variation of the value it describes. Accordingly, in some embodiments, the numerical parameters set forth in the description and attached claims are approximations that may vary depending upon the desired properties sought to be obtained by a particular embodiment. In some embodiments, the numerical parameters should be construed in light of the number of reported significant digits and by applying ordinary rounding techniques. Although the numerical domains and parameters used in the present disclosure are used to confirm its range breadth, in the specific embodiment, the settings of such values are as accurate as possible within the feasible range.

For each patent, patent application, patent application publication, or other materials cited in the present disclosure, such as articles, books, specifications, publications, documents, or the like, the entire contents of which are hereby incorporated into the present disclosure as a reference. Except for the application history documents that are inconsistent with or conflict with the contents of the present disclosure, and the documents that limit the widest range of claims in the present disclosure (currently or later attached to the present disclosure). It should be noted that if a description, definition, and/or terms in the subsequent material of the present disclosure are inconsistent or conflict with the content described in the present disclosure, the use of description, definition, and/or terms in this manual shall prevail.

Finally, it should be understood that the embodiments described in the present disclosure are intended to illustrate the principles of the embodiments of the present disclosure. Other deformations may also belong to the scope of this disclosure. Thus, as an example, not limited, the alternative configuration of the present disclosure embodiment can be consistent with the teachings of the present disclosure. Accordingly, the embodiments of the present disclosure are not limited to the embodiments of the present disclosure clearly described and described.

What is claimed is:

1. A method for data transmission, wherein the method is implemented on a data processing unit of a computed tomography (CT) device, the data processing unit is communicatively connected to a first communication link group and at least one second communication link, and the method comprises:

determining, whether the first communication link group includes at least one failed communication link;

in response to determining that the first communication link group includes at least one failed communication link, selecting, from the at least one second communication link, at least one target communication link matching the at least one failed communication link; and adjusting the first communication link group to a second communication link group, and the second communication link group at least including the at least one target communication link.

2. The method of claim 1, wherein before the first communication link group is adjusted to the second communication link group, a plurality of communication connections are established between the data processing unit and a plurality of data sending units through the first communication link group, and after the first communication link group is adjusted to the second communication link group, the communication connections between the data processing unit and the plurality of data sending units are established through the second communication link group.

3. The method of claim 2, wherein, the first communication link group includes a plurality of first communication links, and the second communication link group further includes one or more first communication links of the plurality of first communication links that are not failed.

4. The method of claim 1, the selecting, from the at least one second communication link, at least one target communication link matching the at least one failed communication link including:

for each of the at least one failed communication link, determining a count of communication links located between the failed communication link and each of the at least one second communication link;

selecting, from the at least one second communication link, a second communication link with a minimum count of communication links; and determining the selected second communication link as the target communication link corresponding to the failed communication link.

5. The method of claim 1, the selecting, from the at least one second communication link, at least one target communication link matching the at least one failed communication link including:

for each of the at least one failed communication link, determining, from the at least one second communication link, at least one selected second communication link connected to a same data processing board with the failed communication link; and determining, based on the at least one selected second communication link, the target communication link matching the failed communication link.

6. The method of claim 5, the determining, based on the at least one selected second communication link, the target communication link matching the failed communication link including:

for each of the at least one selected second communication link, determining a count of communication links located between the failed communication link and the selected second communication link; and designating the selected second link corresponding to a minimum count of communication links as the target communication link corresponding to the failed communication link.

7. The method of claim 1, the adjusting the first communication link group to a second communication link group including:

for each of the at least one failed communication link, obtaining an identification of the target communication link matching the failed communication link; and establishing, based on the identification of the target communication link, a communication connection between the target communication link and a data sending unit that is communicatively connected to the failed communication link.

8. The method of claim 3, the adjusting the first communication link group to a second communication link group including:

for each of the at least one failed communication link, obtaining an identification of the target communication link matching the failed communication link;

determining, based on the identification of the target communication link, a plurality of target data sending units, the plurality of target data sending units being communicatively connected to the failed communication link and one or more first communication links that are located between the failed communication link and the target communication link; and sequentially adjusting the communication links that are communicatively connected to the plurality of target data sending units based on a direction from the target communication link to the failed communication link.

9. The method of claim 2, wherein the plurality of data sending units include a plurality of detector modules of the CT device, and the method further includes:

receiving, through the second communication link group, scan data sent by the plurality of detector modules; and performing data processing on the scan data and sending the processed scan data to an image reconstruction module.

10. The method of claim 9, wherein the scan data includes a plurality of sets of scan data each of which is collected by one of the plurality of detector modules, and the performing data processing on the scan data includes:

obtaining a corresponding relation between each communication link in the second communication link group and the plurality of detector modules;

determining, based on the corresponding relation, a ranking result of the plurality of sets of scan data; and obtaining the processed scan data by processing the sets of scan data based on the ranking result.

11. The method of claim 2, wherein at least one of the plurality of communication connections is established through a short distance non-contact communication mode.

12. The method of claim 11, wherein the data processing unit includes at least two data processing boards, and each of the at least one second communication link is communicatively connected to at least one of the at least two data processing boards.

13. The method of claim 12, wherein for each of the at least one data processing board, a count and/or an arrangement manner of the at least one second communication link that is connected to the data processing board are determined based on a probability that the data processing board has a communication link failure.

14. The method of claim 13, the at least one second communication link includes one or more second communication links that are closer to an edge of the data processing unit than the plurality of first communication links, or the at least one second communication link includes a plurality of second communication links arranged at intervals with the plurality of first communication links.

15. The method of claim 14, wherein a count and/or an arrangement manner of the at least one second communication link are determined based on a probability that a communication link failure occurs, and the probability relates to at least one of an application scenario of the CT device, an equipment type of the CT device, an usage frequency of the CT device, an usage environment of the CT device, connection manners between a plurality of data sending units and the plurality of first communication links, connection manners between the plurality of data sending units and the at least one second communication link, a communication link that has one or more historical failures, a count of the one or more historical failures, or the like, or any combination thereof.

16. The method of claim 15, wherein the probability is determined based on a trained machine learning model.

17. The method of claim 12, wherein different data processing boards of the data processing unit are connected to different counts of second communication links.

18. The method of claim 1, wherein an adjustment manner from the first communication link group to the second communication link group is determined based on connection manners between a plurality of data sending units and the at least one second communication link.

19. A computed tomography (CT) device, comprising:

a scanner configured to scan a target object;

a detector configured to acquire scan data, the detector including a plurality of detector modules;

a data transmission device configured to perform data processing on the scan data; and an image reconstruction unit configured to perform image reconstruction on the processed scan data, so as to generate a scanned image of the target object, wherein the data transmission device include a plurality of communication links and a data processing unit, wherein the data processing unit is communicatively connected to a plurality of first communication links and at least one second communication link, the plurality of first communication links are configured to establish a plurality of communication connections between the data processing unit and the plurality of detector modules, and the at least one second communication link is configured to replace at least one failed communication link when the plurality of first communication links include the at least one failed communication link.

20. A device for data transmission, wherein the device is implemented on a computed tomography (CT) device, and the device comprises:

a data processing unit being communicatively connected to a first communication link group and at least one second communication link, wherein the data processing unit is configured to:

determine whether the first communication link group includes at least one failed communication link;

in response to determining that the first communication link group includes at least one failed communication link, select, from the at least one second communication link, at least one target communication link matching the at least one failed communication link; and adjust the first communication link group to a second communication link group, and the second communication link group at least including the at least one target communication link.

\* \* \* \* \*